(12) United States Patent
Takahashi et al.

(10) Patent No.: US 9,089,136 B2
(45) Date of Patent: Jul. 28, 2015

(54) PYRIMIDINE COMPOUND AND USE THEREOF FOR PEST CONTROL

(75) Inventors: Masaki Takahashi, Takarazuka (JP); Takamasa Tanabe, Takarazuka (JP); Yoshihiko Nokura, Takarazuka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 137 days.

(21) Appl. No.: 13/990,234

(22) PCT Filed: Nov. 30, 2011

(86) PCT No.: PCT/JP2011/078229
§ 371 (c)(1),
(2), (4) Date: May 29, 2013

(87) PCT Pub. No.: WO2012/074135
PCT Pub. Date: Jun. 7, 2012

(65) Prior Publication Data
US 2013/0252981 A1 Sep. 26, 2013

(30) Foreign Application Priority Data
Dec. 1, 2010 (JP) ................................. 2010-268138

(51) Int. Cl.
| | | |
|---|---|---|
| A01N 43/54 | (2006.01) |
| A01N 43/76 | (2006.01) |
| A01N 43/90 | (2006.01) |
| C07D 471/04 | (2006.01) |
| C07D 403/04 | (2006.01) |
| C07D 413/04 | (2006.01) |
| C07D 413/14 | (2006.01) |
| C07D 487/04 | (2006.01) |
| C07D 498/04 | (2006.01) |

(52) U.S. Cl.
CPC ............... *A01N 43/54* (2013.01); *A01N 43/76* (2013.01); *A01N 43/90* (2013.01); *C07D 403/04* (2013.01); *C07D 413/04* (2013.01); *C07D 413/14* (2013.01); *C07D 471/04* (2013.01); *C07D 487/04* (2013.01); *C07D 498/04* (2013.01)

(58) Field of Classification Search
CPC ....... A01N 43/54; A01N 43/76; A01N 43/90; C07D 471/04; C07D 403/04; C07D 413/04; C07D 413/14
USPC ............................ 514/256, 269; 544/333, 298
See application file for complete search history.

(56) References Cited

U.S. PATENT DOCUMENTS 4,690,926 A 9/1987 Saitoh et al.

FOREIGN PATENT DOCUMENTS

| | | |
|---|---|---|
| CA | 2495455 A1 | 3/2004 |
| CA | 2498559 A1 | 3/2004 |
| WO | 2004022057 A1 | 3/2004 |
| WO | 2004022553 A1 | 3/2004 |
| WO | 2008108958 A2 | 9/2008 |
| WO | 2008132434 A2 | 11/2008 |
| WO | 2011049221 A1 | 4/2011 |

OTHER PUBLICATIONS

Office Action issued Aug. 11, 2014 in EP Application No. 11805995.5.
Int'l Search Report and Written Opinion issued Mar. 23, 2012 in Int'l Application No. PCT/JP2011/078229.
Brederick et al, "Synthese von Imidazolinyl-, Benzimidazolyl- und Benzthiazolyl-pyrimidin", Chemische Berichte, vol. 93, No. 10, pp. 2410-2414 (1960).
Int'l Preliminary Report on Patentability issued Jun. 4, 2013 in Int'l Application No. PCT/JP2011/078229.

*Primary Examiner* — James O Wilson
*Assistant Examiner* — Ebenezer O Sackey
(74) *Attorney, Agent, or Firm* — Panitch Schwarze Belisario & Nadel LLP

(57) ABSTRACT

A pyrimidine compound of the formula (1): wherein: $R^1$ represents hydrogen, and the like; $R^2$ represents hydrogen, and the like; $R^3$ represents a C1-C6 chain hydrocarbon group optionally having one or more halogens, and the like; $R^4$ and $R^5$ are represent a C1-C6 chain hydrocarbon group optionally having one or more halogens, and the like; X represents nitrogen, and the like; Y represents nitrogen, and the like; and Z represents oxygen or $-NR^8-$ wherein $R^8$ represents a C1-C6 chain hydrocarbon group optionally having one or more halogens, and the like. The compound has a superior activity of controlling pests.

(1)

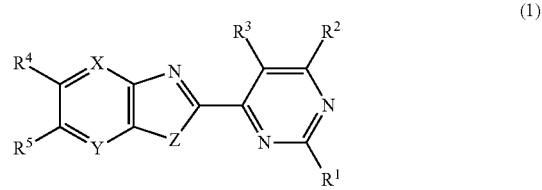

12 Claims, No Drawings

US 9,089,136 B2

PYRIMIDINE COMPOUND AND USE THEREOF FOR PEST CONTROL

CROSS-REFERENCE TO RELATED APPLICATION

This application is a Section 371 of International Application No. PCT/JP2011/078229, filed Nov. 30, 2011, which was published in the English language on Jun. 7, 2012, under International Publication No. WO 2012/074135 A1, and the disclosure of which is incorporated herein by reference.

TECHNICAL FIELD

The present invention relates to a pyrimidine compound and use in pest control thereof.

BACKGROUND ART

Compounds having activity of controlling pests have been found and developed as an active ingredient of a pest controlling agent. Certain pyrimidine compounds are known (see, Patent Literatures 1-2).

CITATION LIST

Patent Literature

Patent Literature 1: U.S. Pat. No. 4,690,926
Patent Literature 2: WO 2008/108958

SUMMARY OF INVENTION

Technical Problem

An object of the present invention is to provide a novel compound having an activity of controlling pests.

Solution to Problem

The present inventors have studied so as to find a compound having an activity of controlling pests and found that a pyrimidine compound of the following formula (1) has an activity of controlling pests, thus leading to the present invention.

That is, the present invention provides:
[1] A pyrimidine compound of the formula (1):

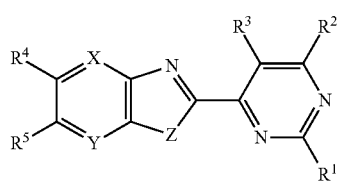

(1)

wherein:
$R^1$ represents hydrogen or halogen,
$R^2$ represents hydrogen or halogen,
$R^3$ represents a C1-C6 chain hydrocarbon group optionally having one or more halogens, a C3-C8 cycloalkyl group optionally having one or more halogens, a C1-C6 alkoxy group optionally having one or more halogens, a C1-C6 alkylthio group optionally having one or more halogens, a C1-C6 alkylsulfinyl group optionally having one or more halogens, a C1-C6 alkylsulfonyl group optionally having one or more halogens, a C1-C6 alkylamino group optionally having one or more halogens, a C2-C8 dialkylamino group optionally having one or more halogens, a C2-C6 alkylcarbonylamino group optionally having one or more halogens, a C2-C6 alkoxycarbonylamino group optionally having one or more halogens, a C2-C6 alkylcarbonyl group optionally having one or more halogens, a C2-C6 alkoxycarbonyl group optionally having one or more halogens, a C2-C6 alkylcarbamoyl group optionally having one or more halogens, a C2-C8 dialkylcarbamoyl group optionally having one or more halogens, a C2-C6 alkoxyalkyl group optionally having one or more halogens, a C2-C6 alkylthioalkyl group optionally having one or more halogens, a phenyl group optionally having one or more atoms or groups selected from Group α, a 5-6 membered aromatic heterocyclic group optionally having one or more atoms or groups selected from Group α, hydrogen, halogen, a hydroxyl group, a mercapto group, an amino group, a nitro group, a cyano group, or a formyl group, $R^4$ and $R^5$ may be same or different and independently represent a C1-C6 chain hydrocarbon group optionally having one or more halogens, a C3-C8 cycloalkyl group optionally having one or more halogens, a C1-C6 alkoxy group optionally having one or more halogens, a C1-C6 alkylthio group optionally having one or more halogens, a C1-C6 alkylsulfinyl group optionally having one or more halogens, a C1-C6 alkylsulfonyl group optionally having one or more halogens, a C1-C6 alkylamino group optionally having one or more halogens, a C2-C8 dialkylamino group optionally having one or more halogens, a C2-C6 alkylcarbonyl group optionally having one or more halogens, a C2-C6 alkoxycarbonyl group optionally having one or more halogens, a phenyl group optionally having one or more atoms or groups selected from Group α, a 5-6 membered aromatic heterocyclic group optionally having one or more atoms or groups selected from Group α, hydrogen, halogen, a hydroxyl group, a mercapto group, an amino group, a nitro group, a cyano group, or a formyl group, provided that both $R^4$ and $R^5$ are not hydrogen; or $R^4$ and $R^5$ may together with the atoms to which they are bonded form a 5- or 6-membered ring having one or more halogens, X represents nitrogen or =CR$^6$— wherein $R^6$ represents hydrogen or halogen,
Y represents nitrogen or =CR$^7$— wherein $R^7$ represents hydrogen or halogen,
Z represents oxygen or —NR$^8$— wherein $R^8$ represents a C1-C6 chain hydrocarbon group optionally having one or more halogens, a C3-C8 cycloalkyl group optionally having one or more halogens, or hydrogen; and
the Group α consists of a C1-C3 alkyl group optionally having one or more halogens, a C1-C3 alkoxy group optionally having one or more halogens, a C1-C3 alkylthio group optionally having one or more halogens, a C1-C3 alkylsulfinyl group optionally having one or more halogens, a C1-C3 alkylsulfonyl group optionally having one or more halogens, halogen, a cyano group, and a nitro group (hereinafter referred to as the present compound);
[2] The pyrimidine compound according to the above [1] wherein $R^1$ is hydrogen, and $R^2$ is hydrogen;
[3] The pyrimidine compound according to the above [1] or [2] wherein $R^3$ is a C1-C6 chain hydrocarbon group optionally having one or more halogens, a C1-C6 alkoxy group optionally having one or more halogens, a C1-C6 alkylthio group optionally having one or more halogens, a C1-C6 alkylsulfinyl group optionally having one or more halogens, a C1-C6 alkylsulfonyl group optionally having one or more halogens, hydrogen, or halogen;

[4] The pyrimidine compound according to the above [1] or [2] wherein $R^3$ is a C1-C3 alkyl group optionally having one or more halogens, a C1-C3 alkoxy group optionally having one or more halogens, a C1-C3 alkylthio group optionally having one or more halogens, a C1-C3 alkylsulfinyl group optionally having one or more halogens, a C1-C3 alkylsulfonyl group optionally having one or more halogens, hydrogen, or halogen;

[5] The pyrimidine compound according to the above [1] or [2] wherein $R^3$ is a C1-C3 alkylthio group optionally having one or more halogens, a C1-C3 alkylsulfinyl group optionally having one or more halogens, or a C1-C3 alkylsulfonyl group optionally having one or more halogens;

[6] The pyrimidine compound according to any one of the above [1]-[5] wherein $R^4$ is a C1-C3 alkyl group optionally having one or more halogens, a C1-C3 alkoxy group optionally having one or more halogens, a C1-C3 alkylthio group optionally having one or more halogens, halogen, a hydroxyl group, a mercapto group, a nitro group, or a cyano group, and $R^5$ is hydrogen;

[7] The pyrimidine compound according to any one of the above [1]-[5] wherein $R^4$ is a C1-C3 alkyl group having one or more fluorines, a C1-C3 alkoxy group having one or more fluorines, a C1-C3 alkylthio group having one or more fluorines, chlorine, or bromine, and $R^5$ is hydrogen;

[8] The pyrimidine compound according to any one of the above [1]-[7] wherein Z is oxygen, X is =$CR^6$—, and $R^6$ is hydrogen;

[9] The pyrimidine compound according to any one of the above [1]-[7] wherein Z is —$NR^8$—, $R^8$ is a methyl group, X is =$CR^6$—, and $R^6$ is hydrogen;

[10] The pyrimidine compound according to any one of the above [1]-[9] wherein Y is nitrogen;

[11] A pest controlling agent comprising the pyrimidine compound according to any one of the above [1]-[10] and an inert carrier;

[12] Use of the pyrimidine compound according to any one of the above [1]-[10] for controlling pests;

[13] A method of controlling pests which comprises the step of applying an effective amount of the pyrimidine compound according to any one of the above [1]-[10] to pests or habitats of pests.

DESCRIPTION OF EMBODIMENTS

In the present compound, examples of the "halogen" include fluorine, chlorine, bromine, and iodine.

Herein, for example, the part "C2-C6" in "a C2-C6 alkoxycarbonyl group" represents that the number of carbon atoms in the whole alkoxycarbonyl group is within a range from 2 to 6.

In the present compound, examples of the "C1-C6 chain hydrocarbon group" include, for example, a C1-C6 alkyl group such as a methyl group, an ethyl group, a propyl group, an isopropyl group, a butyl group, an isobutyl group, a sec-butyl group, a tert-butyl group, a pentyl group, an isopentyl group, a 1-methylbutyl group, a tert-pentyl group, a neopentyl group, a hexyl group, and an isohexyl group;
a C2-C6 alkenyl group such as a vinyl group, a 2-propenyl group, a 2-butenyl group, a 3-butenyl group, a 2-methyl-2-propenyl group, a 3-methyl-2-butenyl group, a 2-pentenyl group, and a 2-hexenyl group; and
a C2-C6 alkynyl group such as an ethynyl group, a 2-propynyl group, a 2-butynyl group, and a 3-butynyl group.

In the present compound, examples of the "C1-C6 chain hydrocarbon group optionally having one or more halogens" include, for example, a C1-C6 alkyl group optionally having one or more halogens such as a methyl group, an ethyl group, a propyl group, an isopropyl group, a butyl group, an isobutyl group, a sec-butyl group, a tert-butyl group, a pentyl group, an isopentyl group, a 1-methylbutyl group, a tert-pentyl group, a neopentyl group, a hexyl group, an isohexyl group, a difluoromethyl group, a trifluoromethyl group, a dichloromethyl group, a trichloromethyl group, a 2,2,2-trifluoroethyl group, a 2,2,2-trichloroethyl group, a pentafluoroethyl group, a perfluoropropyl group, a perfluorobutyl group, and a perfluorohexyl group;
a C2-C6 alkenyl group optionally having one or more halogens such as a vinyl group, a 2-propenyl group, a 3-chloro-2-propenyl group, a 2-chloro-2-propenyl group, a 3,3-dichloro-2-propenyl group, a 2-butenyl group, a 3-butenyl group, a 2-methyl-2-propenyl group, a 3-methyl-2-butenyl group, a 2-pentenyl group, and a 2-hexenyl group; and
a C2-C6 alkynyl group optionally having one or more halogens such as an ethynyl group, a 2-propynyl group, a 2-butynyl group, a 3-butynyl group, a 3-chloro-2-propynyl group, and a 3-bromo-2-propynyl group.

In the present compound, examples of the "C3-C8 cycloalkyl group optionally having one or more halogens" include, for example, a cyclopropyl group, a 2,2-difluorocyclopropyl group, a 2,2-dichlorocyclopropyl group, a 2,2-dibromocyclopropyl group, a cyclobutyl group, a cyclopentyl group, a cyclohexyl group, a cycloheptyl group, and a cyclooctyl group.

In the present compound, examples of the "C1-C6 alkoxy group optionally having one or more halogens" include, for example, a methoxy group, a trifluoromethoxy group, an ethoxy group, a 2,2,2-trifluoroethoxy group, a propyloxy group, an isopropyloxy group, a butoxy group, an isobutyloxy group, a sec-butyloxy group, a tert-butyloxy group, a pentyloxy group, and a hexyloxy group.

In the present compound, examples of the "C1-C6 alkylthio group optionally having one or more halogens" include, for example, a methylthio group, a trifluoromethylthio group, an ethylthio group, a 2,2,2-trifluoroethylthio group, a propylthio group, an isopropylthio group, a butylthio group, an isobutylthio group, a sec-butylthio group, a tert-butylthio group, a pentylthio group, and a hexylthio group.

In the present compound, examples of the "C1-C6 alkylsulfinyl group optionally having one or more halogens" include, for example, a methylsulfinyl group, a trifluoromethylsulfinyl group, an ethylsulfinyl group, a 2,2,2-trifluoroethylsulfinyl group, a propylsulfinyl group, an isopropylsulfinyl group, a butylsulfinyl group, an isobutylsulfinyl group, a sec-butylsulfinyl group, a tert-butylsulfinyl group, a pentylsulfinyl group, and a hexylsulfinyl group.

In the present compound, examples of the "C1-C6 alkylsulfonyl group optionally having one or more halogens" include, for example, a methylsulfonyl group, a trifluoromethylsulfonyl group, and an ethylsulfonyl group.

In the present compound, examples of the "C1-C6 alkylamino group optionally having one or more halogens" include, for example, a methylamino group, an ethylamino group, a 2,2,2-trifluoroethylamino group, a propylamino group, an isopropylamino group, a butylamino group, a pentylamino group, and a hexylamino group.

In the present compound, examples of the "C2-C8 dialkylamino group optionally having one or more halogens" include, for example, a dimethylamino group, a diethylamino group, a bis(2,2,2-trifluoroethyl)amino group, and a dipropylamino group.

In the present compound, examples of the "C2-C6 alkylcarbonylamino group optionally having one or more halogens" include, for example, an acetylamino group, a propionylamino group, a butanoylamino group, a pentanoylamino group, a trifluoroacetylamino group, and a trichloroacetylamino group.

In the present compound, examples of the "C2-C6 alkoxycarbonylamino group optionally having one or more halogens" include, for example, a methoxycarbonylamino group, an ethoxycarbonylamino group, a propoxycarbonylamino group, a tert-butoxycarbonylamino group, and a 2,2,2-trichloroethoxycarbonylamino group.

In the present compound, examples of the "C2-C6 alkylcarbonyl group optionally having one or more halogens" include, for example, an acetyl group, a propionyl group, a butanoyl group, a pentanoyl group, and a trifluoroacetyl group.

In the present compound, examples of the "C2-C6 alkoxycarbonyl group optionally having one or more halogens" include, for example, a methoxycarbonyl group, an ethoxycarbonyl group, a propoxycarbonyl group, a 2,2,2-trifluoroethoxycarbonyl group, and a tert-butoxycarbonyl group.

In the present compound, examples of the "C2-C6 alkylcarbamoyl group optionally having one or more halogens" include, for example, a methylcarbamoyl group, an ethylcarbamoyl group, and a 2,2,2-trifluoroethylcarbamoyl group.

In the present compound, examples of the "C2-C8 dialkylcarbamoyl group optionally having one or more halogens" include, for example, a dimethylcarbamoyl group, a diethylcarbamoyl group, and a dipropylcarbamoyl group.

In the present compound, examples of the "C2-C6 alkoxyalkyl group optionally having one or more halogens" include, for example, a methoxymethyl group, an ethoxymethyl group, a 1-methoxyethyl group, and a 1-(2,2,2-trifluoroethoxy)ethyl group.

In the present compound, examples of the "C2-C6 alkylthioalkyl group optionally having one or more halogens" include, for example, a methylthiomethyl group, an ethylthiomethyl group, a 1-methylthioethyl group, and a trifluoromethylthiomethyl group.

In the present compound, examples of the "phenyl group optionally having one or more atoms or groups selected from Group α" include, for example, a phenyl group, a 2-chlorophenyl group, a 3-chlorophenyl group, a 4-chlorophenyl group, a 2-cyanophenyl group, a 3-cyanophenyl group, a 4-cyanophenyl group, a 2-nitrophenyl group, a 3-nitrophenyl group, a 4-nitrophenyl group, a 2-methylphenyl group, a 3-methylphenyl group, a 4-methylphenyl group, a 2-(trifluoromethyl)phenyl group, a 3-(trifluoromethyl)phenyl group, a 4-(trifluoromethyl)phenyl group, a 2-methoxyphenyl group, a 3-methoxyphenyl group, a 4-methoxyphenyl group, a 2-(methylthio)phenyl group, a 2-(ethylthio)phenyl group, a 2-(ethylsulfinyl)phenyl group, a 2-(ethylsulfonyl)phenyl group, and a 4-(trifluoromethoxy)phenyl group.

In the present compound, examples of the "5-6 membered aromatic heterocyclic group" include a 5-membered aromatic heterocyclic group and a 6-membered aromatic heterocyclic group such as a 2-pyrrolyl group, a 2-furyl group, a 3-furyl group, a 2-thienyl group, a 3-thienyl group, a 5-pyrazolyl group, a 4-pyrazolyl group, a 2-pyridinyl group, a 3-pyridinyl group, a 4-pyridinyl group, a pyrazinyl group, a 1-pyrrolyl group, and a 1-pyrazolyl group.

In the present compound, examples of the "5-6 membered aromatic heterocyclic group optionally having one or more atoms or groups selected from Group α" include a 5-membered aromatic heterocyclic group optionally having one or more atoms or groups selected from Group α and a 6-membered aromatic heterocyclic group optionally having one or more atoms or groups selected from Group α such as a 1-methyl-2-pyrrolyl group, a 2-furyl group, a 3-furyl group, a 5-bromo-2-furyl group, a 5-nitro-2-furyl group, a 2-methyl-3-furyl group, a 2,5-dimethyl-3-furyl group, a 2,4-dimethyl-3-furyl group, a 2-thienyl group, a 3-thienyl group, a 5-methyl-2-thienyl group, a 3-methyl-2-thienyl group, a 1-methyl-3-trifluoromethyl-5-pyrazolyl group, a 5-chloro-1,3-dimethyl-4-pyrazolyl group, a 2-pyridinyl group, a 3-pyridinyl group, a 4-pyridinyl group, a 2-methyl-3-pyridinyl group, a 6-methyl-3-pyridinyl group, a 2-chloro-3-pyridinyl group, a 6-chloro-3-pyridinyl group, a pyrazinyl group, a 1-pyrrolyl group, a 1,2,4-triazole-1-yl group, and a 1-pyrazolyl group.

In the present compound, examples of the compound wherein "$R^4$ and $R^5$ may together with the atom to which they are bonded form a 5- or 6-membered ring having one or more halogens" include, for example, the compounds of the formulae: (a)-(j):

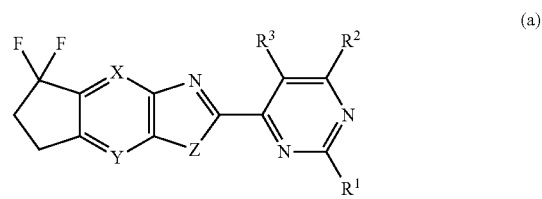

(a)

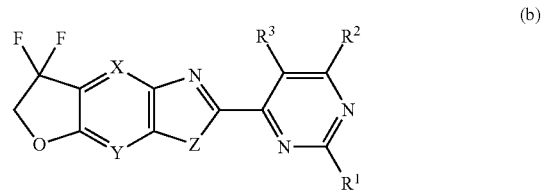

(b)

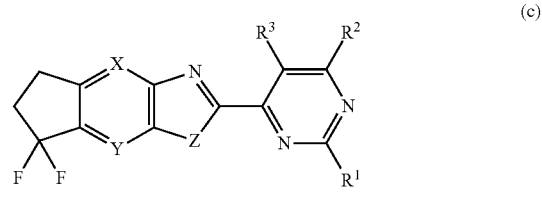

(c)

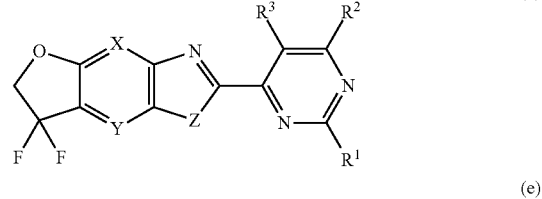

(d)

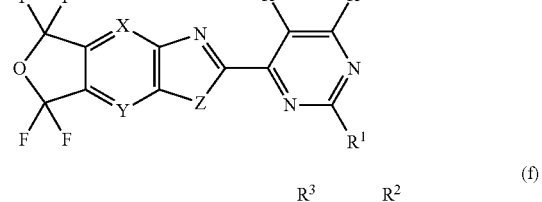

(e)

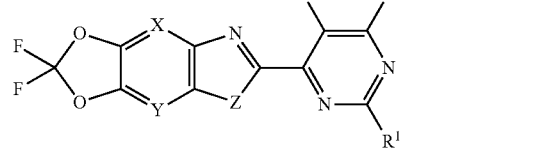

(f)

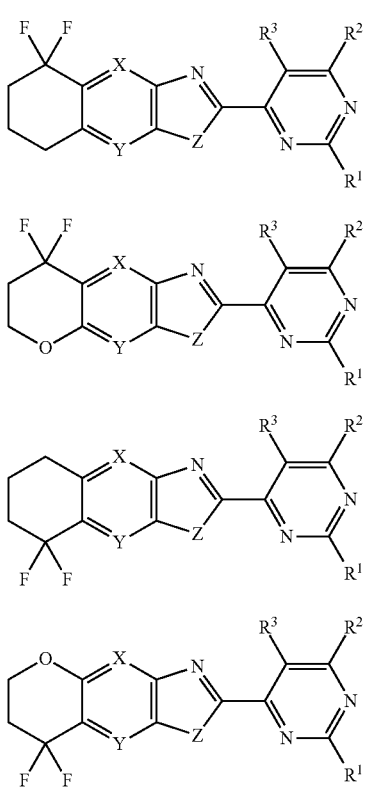

[wherein R¹, R², R³, X, Y, and Z are as defined above].

In the present compound, examples of the "C1-C3 alkyl group optionally having one or more halogens" include, for example, a methyl group, an ethyl group, a propyl group, an isopropyl group, and a 2,2,2-trifluoroethyl group.

In the present compound, examples of the "C1-C3 alkoxy group optionally having one or more halogens" include, for example, a methoxy group, a trifluoromethoxy group, an ethoxy group, a 2,2,2-trifluoroethoxy group, a propyloxy group, and an isopropyloxy group.

In the present compound, examples of the "C1-C3 alkylthio group optionally having one or more halogens" include, for example, a methylthio group, a trifluoromethylthio group, an ethylthio group, a 2,2,2-trifluoroethylthio group, a propylthio group, and an isopropylthio group.

In the present compound, examples of the "C1-C3 alkylsulfinyl group optionally having one or more halogens" include, for example, a methylsulfinyl group, a trifluoromethylsulfinyl group, an ethylsulfinyl group, a 2,2,2-trifluoroethylsulfinyl group, a propylsulfinyl group, and an isopropylsulfinyl group.

In the present compound, examples of the "C1-C3 alkylsulfonyl group optionally having one or more halogens" include, for example, a methylsulfonyl group, a trifluoromethylsulfonyl group, and an ethylsulfonyl group.

In the present compound, examples of the "C1-C3 alkyl group having one or more fluorines" include, for example, a trifluoromethyl group, a pentafluoroethyl group, a heptafluoroisopropyl group, and a 2,2,2-trifluoroethyl group.

In the present compound, examples of the "C1-C3 alkoxy group having one or more fluorines" include, for example, a trifluoromethoxy group, a 2,2,3,3-tetrafluoropropoxy group, and a 2,2,2-trifluoroethoxy group.

In the present compound, examples of the "C1-C3 alkylthio group having one or more fluorines" include, for example, a trifluoromethylthio group, a pentafluoroethylthio group, a heptafluoroisopropylthio group, and a 2,2,2-trifluoroethylthio group.

Examples of the present compound, for example, include the following pyrimidine compounds.

A pyrimidine compound of the formula (1) wherein $R^1$ is hydrogen.

A pyrimidine compound of the formula (1) wherein $R^1$ is halogen.

A pyrimidine compound of the formula (1) wherein $R^2$ is hydrogen.

A pyrimidine compound of the formula (1) wherein $R^2$ is halogen.

A pyrimidine compound of the formula (1) wherein $R^1$ is hydrogen, and $R^2$ is hydrogen.

A pyrimidine compound of the formula (1) wherein $R^3$ is a C1-C6 chain hydrocarbon group optionally having one or more halogens, a C3-C8 cycloalkyl group optionally having one or more halogens, a C1-C6 alkoxy group optionally having one or more halogens, a C1-C6 alkylthio group optionally having one or more halogens, a C1-C6 alkylsulfinyl group optionally having one or more halogens, a C1-C6 alkylsulfonyl group optionally having one or more halogens, a C1-C6 alkylamino group optionally having one or more halogens, a C2-C8 dialkylamino group optionally having one or more halogens, a C2-C6 alkylcarbonylamino group optionally having one or more halogens, a C2-C6 alkoxycarbonylamino group optionally having one or more halogens, a C2-C6 alkylcarbonyl group optionally having one or more halogens, a C2-C6 alkoxycarbonyl group optionally having one or more halogens, a C2-C6 alkylcarbamoyl group optionally having one or more halogens, a C2-C8 dialkylcarbamoyl group optionally having one or more halogens, a C2-C6 alkoxyalkyl group optionally having one or more halogens, a C2-C6 alkylthioalkyl group optionally having one or more halogens, hydrogen, halogen, a hydroxyl group, a mercapto group, an amino group, a nitro group, a cyano group, or a formyl group.

A pyrimidine compound of the formula (1) wherein $R^3$ is a phenyl group optionally having one or more atoms or groups selected from Group α, or a 5-6 membered aromatic heterocyclic group optionally having one or more atoms or groups selected from Group α.

A pyrimidine compound of the formula (1) wherein $R^3$ is a C1-C6 chain hydrocarbon group optionally having one or more halogens, a C1-C6 alkoxy group optionally having one or more halogens, a C1-C6 alkylthio group optionally having one or more halogens, a C1-C6 alkylsulfinyl group optionally having one or more halogens, a C1-C6 alkylsulfonyl group optionally having one or more halogens, a C1-C6 alkylamino group optionally having one or more halogens, a C2-C8 dialkylamino group optionally having one or more halogens, hydrogen, halogen, a hydroxyl group, a mercapto group, an amino group, a nitro group, or a cyano group.

A pyrimidine compound of the formula (1) wherein $R^3$ is a C1-C6 chain hydrocarbon group optionally having one or more halogens, a C1-C6 alkoxy group optionally having one or more halogens, a C1-C6 alkylthio group optionally having one or more halogens, a C1-C6 alkylsulfinyl group optionally having one or more halogens, a C1-C6 alkylsulfonyl group optionally having one or more halogens, hydrogen, or halogen.

A pyrimidine compound of the formula (1) wherein $R^3$ is a C1-C3 alkyl group optionally having one or more halogens, a C1-C3 alkoxy group optionally having one or more halogens, a C1-C3 alkylthio group optionally having one or more halogens, a C1-C3 alkylsulfinyl group optionally having one or more halogens, a C1-C3 alkylsulfonyl group optionally having one or more halogens, hydrogen, or halogen.

A pyrimidine compound of the formula (1) wherein $R^3$ is a C1-C3 alkyl group optionally having one or more halogens, a C1-C3 alkoxy group optionally having one or more halogens, hydrogen, or halogen.

A pyrimidine compound of the formula (1) wherein $R^3$ is a C1-C3 alkylthio group optionally having one or more halogens, a C1-C3 alkylsulfinyl group optionally having one or more halogens, or a C1-C3 alkylsulfonyl group optionally having one or more halogens.

A pyrimidine compound of the formula (1) wherein $R^3$ is a methyl group, an ethyl group, a propyl group, a trifluoromethyl group, a methoxy group, an ethoxy group, a propyloxy group, a trifluoromethoxy group, a 2,2-difluoroethoxy group, a 2,2,2-trifluoroethoxy group, a 2,2,4,4-tetrafluoropropoxy group, a methylthio group, an ethylthio group, a propylthio group, a trifluoromethylthio group, a 2,2,2-trifluoroethylthio group, a methylsulfinyl group, an ethylsulfinyl group, a propylsulfinyl group, a trifluoromethylsulfinyl group, a 2,2,2-trifluoroethylsulfinyl group, a methylsulfonyl group, an ethylsulfonyl group, a propylsulfonyl group, a trifluoromethylsulfonyl group, a 2,2,2-trifluoroethylsulfonyl group, hydrogen, fluorine, chlorine, or bromine.

A pyrimidine compound of the formula (1) wherein $R^3$ is chlorine, an ethyl group, a 2,2,2-trifluoroethoxy group, an ethylthio group, an ethylsulfinyl group, or an ethylsulfonyl group.

A pyrimidine compound of the formula (1) wherein $R^3$ is chlorine.

A pyrimidine compound of the formula (1) wherein $R^3$ is an ethyl group.

A pyrimidine compound of the formula (1) wherein $R^3$ is a 2,2,2-trifluoroethoxy group.

A pyrimidine compound of the formula (1) wherein $R^3$ is an ethylthio group, an ethylsulfinyl group, or an ethylsulfonyl group.

A pyrimidine compound of the formula (1) wherein $R^3$ is an ethylthio group.

A pyrimidine compound of the formula (1) wherein $R^3$ is an ethylsulfinyl group.

A pyrimidine compound of the formula (1) wherein $R^3$ is an ethylsulfonyl group.

A pyrimidine compound of the formula (1) wherein $R^1$ is hydrogen, $R^2$ is hydrogen, and $R^3$ is a C1-C3 alkyl group optionally having one or more halogens, a C1-C3 alkoxy group optionally having one or more halogens, a C1-C3 alkylthio group optionally having one or more halogens, a C1-C3 alkylsulfinyl group optionally having one or more halogens, a C1-C3 alkylsulfonyl group optionally having one or more halogens, hydrogen, or halogen.

A pyrimidine compound of the formula (1) wherein $R^1$ is hydrogen, $R^2$ is hydrogen, and $R^3$ is a C1-C3 alkyl group optionally having one or more halogens, a C1-C3 alkoxy group optionally having one or more halogens, hydrogen, or halogen.

A pyrimidine compound of the formula (1) wherein $R^1$ is hydrogen, $R^2$ is hydrogen, and $R^3$ is a C1-C3 alkylthio group optionally having one or more halogens, a C1-C3 alkylsulfinyl group optionally having one or more halogens, or a C1-C3 alkylsulfonyl group optionally having one or more halogens.

A pyrimidine compound of the formula (1) wherein $R^1$ is hydrogen, $R^2$ is hydrogen, and $R^3$ is a methyl group, an ethyl group, a propyl group, a trifluoromethyl group, a methoxy group, an ethoxy group, a propyloxy group, a trifluoromethoxy group, a 2,2-difluoroethoxy group, a 2,2,2-trifluoroethoxy group, a 2,2,4,4-tetrafluoropropoxy group, a methylthio group, an ethylthio group, a propylthio group, a trifluoromethylthio group, a 2,2,2-trifluoroethylthio group, a methylsulfinyl group, an ethylsulfinyl group, a propylsulfinyl group, a trifluoromethylsulfinyl group, a 2,2,2-trifluoroethylsulfinyl group, a methylsulfonyl group, an ethylsulfonyl group, a propylsulfonyl group, a trifluoromethylsulfonyl group, a 2,2,2-trifluoroethylsulfonyl group, hydrogen, fluorine, chlorine, or bromine.

A pyrimidine compound of the formula (1) wherein $R^1$ is hydrogen, $R^2$ is hydrogen, $R^3$ is a methyl group, an ethyl group, a propyl group, a trifluoromethyl group, a methoxy group, an ethoxy group, a propyloxy group, a trifluoromethoxy group, a 2,2-difluoroethoxy group, a 2,2,2-trifluoroethoxy group, a 2,2,4,4-tetrafluoropropoxy group, hydrogen, fluorine, chlorine, or bromine.

A pyrimidine compound of the formula (1) wherein $R^1$ is hydrogen, $R^2$ is hydrogen, and $R^3$ is a methylthio group, an ethylthio group, a propylthio group, a trifluoromethylthio group, a 2,2,2-trifluoroethylthio group, a methylsulfinyl group, an ethylsulfinyl group, a propylsulfinyl group, a trifluoromethylsulfinyl group, a 2,2,2-trifluoroethylsulfinyl group, a methylsulfonyl group, an ethylsulfonyl group, a propylsulfonyl group, a trifluoromethylsulfonyl group, or a 2,2,2-trifluoroethylsulfonyl group.

A pyrimidine compound of the formula (1) wherein $R^1$ is hydrogen, $R^2$ is hydrogen, and $R^3$ is chlorine, an ethyl group, or a 2,2,2-trifluoroethoxy group.

A pyrimidine compound of the formula (1) wherein $R^1$ is hydrogen, $R^2$ is hydrogen, and $R^3$ is an ethylthio group, an ethylsulfinyl group, or an ethylsulfonyl group.

A pyrimidine compound of the formula (1) wherein $R^1$ is hydrogen, $R^2$ is hydrogen, and $R^3$ is chlorine.

A pyrimidine compound of the formula (1) wherein $R^1$ is hydrogen, $R^2$ is hydrogen, and $R^3$ is an ethylthio group.

A pyrimidine compound of the formula (1) wherein $R^1$ is hydrogen, $R^2$ is hydrogen, and $R^3$ is an ethylsulfinyl group.

A pyrimidine compound of the formula (1) wherein $R^1$ is hydrogen, $R^2$ is hydrogen, and $R^3$ is an ethylsulfonyl group.

A pyrimidine compound of the formula (1) wherein $R^4$ and $R^5$ may be same or different, and independently represent, a C1-C6 chain hydrocarbon group optionally having one or more halogens, a C3-C8 cycloalkyl group optionally having one or more halogens, a C1-C6 alkoxy group optionally having one or more halogens, a C1-C6 alkylthio group optionally having one or more halogens, a C1-C6 alkylsulfinyl group optionally having one or more halogens, a C1-C6 alkylsulfonyl group optionally having one or more halogens, a C1-C6 alkylamino group optionally having one or more halogens, a C2-C8 dialkylamino group optionally having one or more halogens, a C2-C6 alkylcarbonyl group optionally having one or more halogens, a C2-C6 alkoxycarbonyl group optionally having one or more halogens, hydrogen, halogen, a hydroxyl group, a mercapto group, an amino group, a nitro group, a cyano group, or a formyl group.

A pyrimidine compound of the formula (1) wherein $R^4$ and $R^5$ may be same or different, and independently represent a phenyl group optionally having one or more atoms or groups selected from Group α, a 5-6 membered aromatic heterocyclic group optionally having one or more atoms or groups selected from Group α, or hydrogen; or $R^4$ and $R^5$ may together with the atom to which they are bonded form a 5- or 6-membered ring having one or more halogens.

A pyrimidine compound of the formula (1) wherein $R^4$ is a C1-C6 chain hydrocarbon group optionally having one or more halogens, a C1-C6 alkoxy group optionally having one or more halogens, a C1-C6 alkylthio group optionally having one or more halogens, a C1-C6 alkylsulfinyl group optionally having one or more halogens, a C1-C6 alkylsulfonyl group optionally having one or more halogens, a C2-C6 alkylcarbonyl group optionally having one or more halogens, a C2-C6 alkoxycarbonyl group optionally having one or more halogens, halogen, a hydroxyl group, a mercapto group, a nitro group, a cyano group, or a formyl group.

A pyrimidine compound of the formula (1) wherein $R^4$ is a C1-C6 chain hydrocarbon group optionally having one or more halogens, a C1-C6 alkoxy group optionally having one or more halogens, a C1-C6 alkylthio group optionally having one or more halogens, a C1-C6 alkylsulfinyl group optionally having one or more halogens, a C1-C6 alkylsulfonyl group optionally having one or more halogens, halogen, a hydroxyl group, a mercapto group, a nitro group, or a cyano group.

A pyrimidine compound of the formula (1) wherein $R^4$ is a C1-C3 alkyl group optionally having one or more halogens, a C1-C3 alkoxy group optionally having one or more halogens, a C1-C3 alkylthio group optionally having one or more halogens, halogen, a hydroxyl group, a mercapto group, a nitro group, or a cyano group.

A pyrimidine compound of the formula (1) wherein $R^4$ is a C1-C3 alkyl group optionally having one or more halogens, a C1-C3 alkoxy group optionally having one or more halogens, a C1-C3 alkylthio group optionally having one or more halogens, halogen, or a cyano group.

A pyrimidine compound of the formula (1) wherein $R^4$ is a C1-C3 alkyl group optionally having one or more halogens or a C1-C3 alkoxy group optionally having one or more halogens.

A pyrimidine compound of the formula (1) wherein $R^4$ is a C1-C6 chain hydrocarbon group optionally having one or more halogens.

A pyrimidine compound of the formula (1) wherein $R^4$ is a C1-C3 alkyl group optionally having one or more halogens.

A pyrimidine compound of the formula (1) wherein $R^4$ is a C1-C3 alkoxy group optionally having one or more halogens.

A pyrimidine compound of the formula (1) wherein $R^4$ is a C1-C3 alkylthio group optionally having one or more halogens.

A pyrimidine compound of the formula (1) wherein $R^4$ is a C1-C3 alkylsulfinyl group optionally having one or more halogens.

A pyrimidine compound of the formula (1) wherein $R^4$ is a C1-C3 alkylsulfonyl group optionally having one or more halogens.

A pyrimidine compound of the formula (1) wherein $R^4$ is a C1-C3 alkyl group having one or more fluorines, a C1-C3 alkoxy group having one or more fluorines, a C1-C3 alkylthio group having one or more fluorines, chlorine, or bromine.

A pyrimidine compound of the formula (1) wherein $R^4$ is a C1-C3 alkyl group having one or more fluorines.

A pyrimidine compound of the formula (1) wherein $R^4$ is a C1-C3 alkoxy group having one or more fluorines.

A pyrimidine compound of the formula (1) wherein $R^4$ is a C1-C3 alkylthio group having one or more fluorines.

A pyrimidine compound of the formula (1) wherein $R^4$ is a C1-C3 alkylsulfinyl group optionally having one or more fluorines.

A pyrimidine compound of the formula (1) wherein $R^4$ is a C1-C3 alkylsulfonyl group optionally having one or more fluorines.

A pyrimidine compound of the formula (1) wherein $R^4$ is a trifluoromethyl group, a pentafluoroethyl group, a trifluoromethoxy group, a 2,2-difluoroethoxy group, a 2,2,2-trifluoroethoxy group, a trifluoromethylthio group, a trifluoromethylsulfinyl group, a trifluoromethylsulfonyl group, chlorine, bromine, or iodine.

A pyrimidine compound of the formula (1) wherein $R^4$ is a trifluoromethyl group, a pentafluoroethyl group, a trifluoromethylthio group, a trifluoromethylsulfinyl group, or a trifluoromethylsulfonyl group.

A pyrimidine compound of the formula (1) wherein $R^4$ is a trifluoromethyl group, a trifluoromethoxy group, a 2,2-difluoroethoxy group, a 2,2,2-trifluoroethoxy group, chlorine, or bromine.

A pyrimidine compound of the formula (1) wherein $R^4$ is a trifluoromethyl group.

A pyrimidine compound of the formula (1) wherein $R^4$ is a pentafluoroethyl group.

A pyrimidine compound of the formula (1) wherein $R^4$ is a trifluoromethylthio group.

A pyrimidine compound of the formula (1) wherein $R^4$ is a trifluoromethylsulfinyl group.

A pyrimidine compound of the formula (1) wherein $R^4$ is a trifluoromethylsulfonyl group.

A pyrimidine compound of the formula (1) wherein $R^4$ is hydrogen.

A pyrimidine compound of the formula (1) wherein $R^5$ is a C1-C6 chain hydrocarbon group optionally having one or more halogens, a C1-C6 alkoxy group optionally having one or more halogens, a C1-C6 alkylthio group optionally having one or more halogens, a C1-C6 alkylsulfinyl group optionally having one or more halogens, a C1-C6 alkylsulfonyl group optionally having one or more halogens, a C2-C6 alkylcarbonyl group optionally having one or more halogens, a C2-C6 alkoxycarbonyl group optionally having one or more halogens, hydrogen, halogen, a hydroxyl group, a mercapto group, a nitro group, a cyano group, or a formyl group.

A pyrimidine compound of the formula (1) wherein $R^5$ is a C1-C6 chain hydrocarbon group optionally having one or more halogens, a C1-C6 alkoxy group optionally having one or more halogens, a C1-C6 alkylthio group optionally having one or more halogens, a C1-C6 alkylsulfinyl group optionally having one or more halogens, a C1-C6 alkylsulfonyl group optionally having one or more halogens, hydrogen, halogen, a hydroxyl group, a mercapto group, a nitro group, or a cyano group.

A pyrimidine compound of the formula (1) wherein $R^5$ is a C1-C3 alkyl group optionally having one or more halogens, a C1-C3 alkoxy group optionally having one or more halogens, a C1-C3 alkylthio group optionally having one or more halogens, halogen, a hydroxyl group, a mercapto group, a nitro group, or a cyano group.

A pyrimidine compound of the formula (1) wherein $R^5$ is a C1-C3 alkyl group optionally having one or more halogens, a C1-C3 alkoxy group optionally having one or more halogens, a C1-C3 alkylthio group optionally having one or more halogens, halogen, or a cyano group.

A pyrimidine compound of the formula (1) wherein $R^5$ is a C1-C3 alkyl group optionally having one or more halogens or a C1-C3 alkoxy group optionally having one or more halogens.

A pyrimidine compound of the formula (1) wherein $R^5$ is a C1-C3 alkyl group optionally having one or more halogens.

A pyrimidine compound of the formula (1) wherein $R^5$ is a C1-C3 alkoxy group optionally having one or more halogens.

A pyrimidine compound of the formula (1) wherein $R^5$ is a C1-C3 alkyl group having one or more fluorines, a C1-C3 alkoxy group having one or more fluorines, a C1-C3 alkylthio group having one or more fluorines, chlorine, or bromine.

A pyrimidine compound of the formula (1) wherein $R^5$ is a C1-C3 alkyl group having one or more fluorines.

A pyrimidine compound of the formula (1) wherein $R^5$ is a C1-C3 alkoxy group having one or more fluorines.

A pyrimidine compound of the formula (1) wherein $R^5$ is a C1-C3 alkylthio group having one or more fluorines.

A pyrimidine compound of the formula (1) wherein $R^5$ is a trifluoromethyl group, a trifluoromethoxy group, a 2,2-difluoroethoxy group, a 2,2,2-trifluoroethoxy group, chlorine, or bromine.

A pyrimidine compound of the formula (1) wherein $R^5$ is a trifluoromethyl group.

A pyrimidine compound of the formula (1) wherein $R^5$ is hydrogen.

A pyrimidine compound of the formula (1) wherein $R^4$ is a C1-C3 alkyl group optionally having one or more halogens, a C1-C3 alkoxy group optionally having one or more halogens, a C1-C3 alkylthio group optionally having one or more halogens, a C1-C3 alkylsulfinyl group optionally having one or more halogens, or a C1-C3 alkylsulfonyl group optionally having one or more halogens, and $R^5$ is hydrogen.

A pyrimidine compound of the formula (1) wherein $R^4$ is a C1-C3 alkyl group optionally having one or more halogens, a C1-C3 alkoxy group optionally having one or more halogens, a C1-C3 alkylthio group optionally having one or more halogens, halogen, a hydroxyl group, a mercapto group, a nitro group, or a cyano group, and $R^5$ is hydrogen.

A pyrimidine compound of the formula (1) wherein $R^4$ is hydrogen, and $R^5$ is a C1-C3 alkyl group optionally having one or more halogens, a C1-C3 alkoxy group optionally having one or more halogens, a C1-C3 alkylthio group optionally having one or more halogens, halogen, a hydroxyl group, a mercapto group, a nitro group, or a cyano group.

A pyrimidine compound of the formula (1) wherein $R^4$ is a C1-C3 alkyl group having one or more fluorines, a C1-C3 alkoxy group having one or more fluorines, a C1-C3 alkylthio group having one or more fluorines, a C1-C3 alkylsulfinyl group having one or more fluorines, or a C1-C3 alkylsulfonyl group having one or more fluorines, and $R^5$ is hydrogen.

A pyrimidine compound of the formula (1) wherein $R^4$ is a C1-C3 alkyl group having one or more fluorines, a C1-C3 alkoxy group having one or more fluorines, a C1-C3 alkylthio group having one or more fluorines, chlorine, or bromine, and $R^5$ is hydrogen.

A pyrimidine compound of the formula (1) wherein $R^4$ is a C1-C3 alkyl group having one or more fluorines, and $R^5$ is hydrogen.

A pyrimidine compound of the formula (1) wherein $R^4$ is a C1-C3 alkylthio group having one or more fluorines, and $R^5$ is hydrogen.

A pyrimidine compound of the formula (1) wherein $R^4$ is a C1-C3 alkylsulfinyl group having one or more fluorines, and $R^5$ is hydrogen.

A pyrimidine compound of the formula (1) wherein $R^4$ is a C1-C3 alkylsulfonyl group having one or more fluorines, and $R^5$ is hydrogen.

A pyrimidine compound of the formula (1) wherein $R^5$ is a C1-C3 alkyl group having one or more fluorines, a C1-C3 alkoxy group having one or more fluorines, a C1-C3 alkylthio group having one or more fluorines, chlorine, or bromine, and $R^4$ is hydrogen.

A pyrimidine compound of the formula (1) wherein $R^4$ is a trifluoromethyl group, a pentafluoroethyl group, a trifluoromethoxy group, a 2,2-difluoroethoxy group, a 2,2,2-difluoroethoxy group, a trifluoromethylthio group, a trifluoromethylsulfinyl group, a trifluoromethylsulfonyl group, chlorine, bromine, or iodine, and $R^5$ is hydrogen.

A pyrimidine compound of the formula (1) wherein $R^4$ is a trifluoromethyl group, a pentafluoroethyl group, a trifluoromethylthio group, a trifluoromethylsulfinyl group, or a trifluoromethylsulfonyl group, and $R^5$ is hydrogen.

A pyrimidine compound of the formula (1) wherein $R^4$ is a trifluoromethyl group, and $R^5$ is hydrogen.

A pyrimidine compound of the formula (1) wherein $R^4$ is a pentafluoroethyl group, and $R^5$ is hydrogen.

A pyrimidine compound of the formula (1) wherein $R^4$ is a trifluoromethylthio group, and $R^5$ is hydrogen.

A pyrimidine compound of the formula (1) wherein $R^4$ is a trifluoromethylsulfinyl group, and $R^5$ is hydrogen.

A pyrimidine compound of the formula (1) wherein $R^4$ is a trifluoromethylsulfonyl group, and $R^5$ is hydrogen.

A pyrimidine compound of the formula (1) wherein $R^4$ is bromine, and $R^5$ is hydrogen.

A pyrimidine compound of the formula (1) wherein $R^4$ is iodine, and $R^5$ is hydrogen.

A pyrimidine compound of the formula (1) wherein $R^4$ is a trifluoromethyl group, a trifluoromethoxy group, a 2,2-difluoroethoxy group, a 2,2,2-trifluoroethoxy group, chlorine, or bromine, and $R^5$ is hydrogen.

A pyrimidine compound of the formula (1) wherein $R^4$ is hydrogen, and $R^5$ is a trifluoromethyl group, a trifluoromethoxy group, a 2,2-difluoroethoxy group, a 2,2,2-trifluoroethoxy group, chlorine, or bromine.

A pyrimidine compound of the formula (1) wherein $R^4$ is a C1-C6 chain hydrocarbon group optionally having one or more halogens, and $R^5$ is hydrogen.

A pyrimidine compound of the formula (1) wherein X is nitrogen.

A pyrimidine compound of the formula (1) wherein X is $=CR^6-$, and $R^6$ is hydrogen or halogen.

A pyrimidine compound of the formula (1) wherein X is $=CR^6-$, and $R^6$ is hydrogen.

A pyrimidine compound of the formula (1) wherein X is nitrogen or $=CR^6-$, and $R^6$ is hydrogen.

A pyrimidine compound of the formula (1) wherein Y is nitrogen.

A pyrimidine compound of the formula (1) wherein Y is $=CR^7-$, and $R^7$ is hydrogen or halogen.

A pyrimidine compound of the formula (1) wherein Y is $=CR^7-$, and $R^7$ is hydrogen.

A pyrimidine compound of the formula (1) wherein Y is nitrogen or $=CR^7-$, and $R^7$ is hydrogen.

A pyrimidine compound of the formula (1) wherein X is nitrogen, and Y is nitrogen.

A pyrimidine compound of the formula (1) wherein X is $=CR^6-$, $R^6$ is hydrogen, Y is $=CR^7-$, and $R^7$ is hydrogen or halogen.

A pyrimidine compound of the formula (1) wherein X is $=CR^6-$, $R^6$ is hydrogen, and Y is nitrogen.

A pyrimidine compound of the formula (1) wherein X is nitrogen, Y is $=CR^7-$, and $R^7$ is hydrogen or halogen.

A pyrimidine compound of the formula (1) wherein X is $=CR^6-$, and $R^6$ is hydrogen.

A pyrimidine compound of the formula (1) wherein X is $=CR^6-$, $R^6$ is hydrogen, Y is nitrogen or $=CR^7-$, and $R^7$ is hydrogen.

A pyrimidine compound of the formula (1) wherein X is $=CR^6-$, $R^6$ is hydrogen, $R^4$ is a C1-C3 alkyl group optionally having one or more halogens, a C1-C3 alkoxy group optionally having one or more halogens, a C1-C3 alkylthio group optionally having one or more halogens, halogen, a hydroxyl group, a mercapto group, a nitro group, or a cyano group, and $R^5$ is hydrogen.

A pyrimidine compound of the formula (1) wherein X is $=CR^6-$, $R^6$ is hydrogen, $R^4$ is a C1-C3 alkyl group having one or more fluorines, a C1-C3 alkoxy group having one or more fluorines, a C1-C3 alkylthio group having one or more fluorines, chlorine, or bromine, and $R^5$ is hydrogen.

A pyrimidine compound of the formula (1) wherein X is $=CR^6-$, $R^6$ is hydrogen, $R^4$ is a trifluoromethyl group, a trifluoromethoxy group, a 2,2-difluoroethoxy group, a 2,2,2-trifluoroethoxy group, chlorine, or bromine, and $R^5$ is hydrogen.

A pyrimidine compound of the formula (1) wherein X is $=CR^6-$, $R^6$ is hydrogen, Y is nitrogen, $R^4$ is a C1-C3 alkyl group optionally having one or more halogens, a C1-C3 alkoxy group optionally having one or more halogens, a C1-C3 alkylthio group optionally having one or more halogens, halogen, a hydroxyl group, a mercapto group, a nitro group, or a cyano group, and $R^5$ is hydrogen.

A pyrimidine compound of the formula (1) wherein X is $=CR^6$—, $R^6$ is hydrogen, Y is nitrogen, $R^4$ is a C1-C3 alkyl group having one or more fluorines, a C1-C3 alkoxy group having one or more fluorines, a C1-C3 alkylthio group having one or more fluorines, chlorine, or bromine, $R^5$ is hydrogen.

A pyrimidine compound of the formula (1) wherein X is $=CR^6$—, $R^6$ is hydrogen, Y is nitrogen, $R^4$ is a trifluoromethyl group, a trifluoromethoxy group, a 2,2-difluoroethoxy group, a 2,2,2-trifluoroethoxy group, chlorine, or bromine, and $R^5$ is hydrogen.

A pyrimidine compound of the formula (1) wherein X is $=CR^6$—, $R^6$ is hydrogen, Y is $=CR^7$—, $R^7$ is hydrogen or halogen, $R^4$ is a C1-C3 alkyl group optionally having one or more halogens, a C1-C3 alkoxy group optionally having one or more halogens, a C1-C3 alkylthio group optionally having one or more halogens, halogen, a hydroxyl group, a mercapto group, a nitro group, or a cyano group, $R^5$ is hydrogen.

A pyrimidine compound of the formula (1) wherein X is $=CR^6$—, $R^6$ is hydrogen, Y is $=CR^7$—, $R^7$ is hydrogen or halogen, $R^4$ is a C1-C3 alkyl group having one or more fluorines, a C1-C3 alkoxy group having one or more fluorines, a C1-C3 alkylthio group having one or more fluorines, chlorine, or bromine, and $R^5$ is hydrogen.

A pyrimidine compound of the formula (1) wherein X is $=CR^6$—, $R^6$ is hydrogen, Y is $=CR^7$—, $R^7$ is hydrogen or halogen, $R^4$ is a trifluoromethyl group, a trifluoromethoxy group, a 2,2-difluoroethoxy group, a 2,2,2-trifluoroethoxy group, chlorine, or bromine, and $R^5$ is hydrogen.

A pyrimidine compound of the formula (1) wherein Z is oxygen.

A pyrimidine compound of the formula (1) wherein Z is —$NR^8$—, $R^8$ is hydrogen, a C1-C6 chain hydrocarbon group optionally having one or more halogens, or a C3-C8 cycloalkyl group optionally having one or more halogens.

A pyrimidine compound of the formula (1) wherein Z is —$NR^8$—, and $R^8$ is a C1-C6 chain hydrocarbon group optionally having one or more halogens.

A pyrimidine compound of the formula (1) wherein Z is —$NR^8$—, and $R^8$ is a C1-C3 alkyl group optionally having one or more halogens.

A pyrimidine compound of the formula (1) wherein Z is —$NR^8$—, and $R^8$ is a methyl group, an ethyl group, or a cyclopropyl group.

A pyrimidine compound of the formula (1) wherein Z is —$NR^8$—, and $R^8$ is a methyl group.

A pyrimidine compound of the formula (1) wherein Z is oxygen or —$NR^8$—, and $R^8$ is a C1-C3 alkyl group optionally having one or more halogens.

A pyrimidine compound of the formula (1) wherein Z is oxygen or —$NR^8$—, and $R^8$ is a methyl group, an ethyl group, or a cyclopropyl group.

A pyrimidine compound of the formula (1) wherein Z is oxygen or —$NR^8$—, and $R^8$ is a methyl group.

A pyrimidine compound of the formula (1) wherein X is $=CR^6$—, $R^6$ is hydrogen, Y is nitrogen, and Z is oxygen.

A pyrimidine compound of the formula (1) wherein X is $=CR^6$—, $R^6$ is hydrogen, Y is $=CR^7$—, $R^7$ is hydrogen, and Z is oxygen.

A pyrimidine compound of the formula (1) wherein X is $=CR^6$—, $R^6$ is hydrogen, Y is nitrogen, Z is —$NR^8$—, and $R^8$ is a methyl group.

A pyrimidine compound of the formula (1) wherein X is $=CR^6$—, $R^6$ is hydrogen, Y is $=CR^7$—, $R^7$ is hydrogen, Z is —$NR^8$—, and $R^8$ is a methyl group.

A pyrimidine compound of the formula (1) wherein Z is oxygen or —$NR^8$, $R^8$ is a methyl group, X is $=CR^6$—, $R^6$ is hydrogen, and $R^4$ is a C1-C3 alkyl group optionally having one or more halogens, a C1-C3 alkoxy group optionally having one or more halogens, a C1-C3 alkylthio group optionally having one or more halogens, halogen, a hydroxyl group, a mercapto group, a nitro group, or a cyano group, and $R^5$ is hydrogen.

A pyrimidine compound of the formula (1) wherein Z is oxygen or —$NR^8$—, $R^8$ is a methyl group, X is $=CR^6$—, $R^6$ is hydrogen, $R^4$ is a trifluoromethyl group, a trifluoromethoxy group, a 2,2-difluoroethoxy group, a 2,2,2-trifluoroethoxy group, chlorine, or bromine, and $R^5$ is hydrogen.

A pyrimidine compound of the formula (1) wherein Z is oxygen or —$NR^8$—, $R^8$ is a methyl group, X is $=CR^6$—, $R^6$ is hydrogen, Y is nitrogen, $R^4$ is a C1-C3 alkyl group optionally having one or more halogens, a C1-C3 alkoxy group optionally having one or more halogens, a C1-C3 alkylthio group optionally having one or more halogens, halogen, a hydroxyl group, a mercapto group, a nitro group, or a cyano group, and $R^5$ is hydrogen.

A pyrimidine compound of the formula (1) wherein Z is oxygen or —$NR^8$—, $R^8$ is a methyl group, X is $=CR^6$—, $R^6$ is hydrogen, Y is $=CR^7$—, $R^7$ is hydrogen or halogen, $R^4$ is a C1-C3 alkyl group optionally having one or more halogens, a C1-C3 alkoxy group optionally having one or more halogens, a C1-C3 alkylthio group optionally having one or more halogens, halogen, a hydroxyl group, a mercapto group, a nitro group, or a cyano group, and $R^5$ is hydrogen.

A pyrimidine compound of the formula (1) wherein Z is oxygen, X is $=CR^6$—, $R^6$ is hydrogen, $R^4$ is a C1-C3 alkyl group optionally having one or more halogens, a C1-C3 alkoxy group optionally having one or more halogens, a C1-C3 alkylthio group optionally having one or more halogens, halogen, a hydroxyl group, a mercapto group, a nitro group, or a cyano group, and $R^5$ is hydrogen.

A pyrimidine compound of the formula (1) wherein Z is —$NR^8$—, $R^8$ is a methyl group, X is $=CR^6$—, $R^6$ is hydrogen, $R^4$ is a C1-C3 alkyl group optionally having one or more halogens, a C1-C3 alkoxy group optionally having one or more halogens, a C1-C3 alkylthio group optionally having one or more halogens, halogen, a hydroxyl group, a mercapto group, a nitro group, or a cyano group, and $R^5$ is hydrogen.

A pyrimidine compound of the formula (1) wherein Z is oxygen, X is $=CR^6$—, $R^6$ is hydrogen, $R^4$ is a C1-C3 alkyl group having one or more fluorines, a C1-C3 alkoxy group having one or more fluorines, a C1-C3 alkylthio group having one or more fluorines, chlorine, or bromine, and $R^5$ is hydrogen.

A pyrimidine compound of the formula (1) wherein Z is —$NR^8$—, $R^8$ is a methyl group, X is $=CR^6$—, $R^6$ is hydrogen, $R^4$ is a C1-C3 alkyl group having one or more fluorines, a C1-C3 alkoxy group having one or more fluorines, a C1-C3 alkylthio group having one or more fluorines, chlorine, or bromine, and $R^5$ is hydrogen.

A pyrimidine compound of the formula (1) wherein $R^3$ is a C1-C6 chain hydrocarbon group optionally having one or more halogens, a C1-C6 alkoxy group optionally having one or more halogens, a C1-C6 alkylthio group optionally having one or more halogens, a C1-C6 alkylsulfinyl group optionally having one or more halogens, a C1-C6 alkylsulfonyl group optionally having one or more halogens, hydrogen, or halogen.

A pyrimidine compound of the formula (1) wherein $R^1$ is hydrogen, $R^2$ is hydrogen, $R^3$ is a C1-C6 chain hydrocarbon group optionally having one or more halogens, a C1-C6 alkoxy group optionally having one or more halogens, a C1-C6 alkylthio group optionally having one or more halogens, a C1-C6 alkylsulfinyl group optionally having one or more halogens, a C1-C6 alkylsulfonyl group optionally having one or more halogens, hydrogen, or halogen.

A pyrimidine compound of the formula (1) wherein $R^1$ is hydrogen, $R^2$ is hydrogen, $R^3$ is a C1-C6 chain hydrocarbon group optionally having one or more halogens, a C1-C6 alkoxy group optionally having one or more halogens, a C1-C6 alkylthio group optionally having one or more halogens, a C1-C6 alkylsulfinyl group optionally having one or more halogens, a C1-C6 alkylsulfonyl group optionally having one or more halogens, hydrogen, or halogen, $R^4$ is a C1-C6 chain hydrocarbon group optionally having one or more halogens, and $R^5$ is hydrogen.

A pyrimidine compound of the formula (1) wherein $R^1$ is hydrogen, $R^2$ is hydrogen, $R^3$ is a C1-C6 chain hydrocarbon group optionally having one or more halogens, a C1-C6 alkoxy group optionally having one or more halogens, a C1-C6 alkylthio group optionally having one or more halogens, a C1-C6 alkylsulfinyl group optionally having one or more halogens, a C1-C6 alkylsulfonyl group optionally having one or more halogens, hydrogen, or halogen, $R^4$ is a C1-C6 chain hydrocarbon group optionally having one or more halogens, $R^5$ is hydrogen, X is $=CR^6-$, $R^6$ is hydrogen, Y is nitrogen or $=CR^7-$, $R^7$ is hydrogen, Z is oxygen or $-NR^8-$, and $R^8$ is a C1-C6 chain hydrocarbon group optionally having one or more halogens.

A pyrimidine compound of the formula (1) wherein $R^1$ is hydrogen, $R^2$ is hydrogen, $R^3$ is a C1-C3 alkyl group optionally having one or more halogens, a C1-C3 alkoxy group optionally having one or more halogens, a C1-C3 alkylthio group optionally having one or more halogens, a C1-C3 alkylsulfinyl group optionally having one or more halogens, a C1-C3 alkylsulfonyl group optionally having one or more halogens, hydrogen, or halogen, Z is oxygen or $-NR^8-$, $R^8$ is a methyl group, X is $=CR^6-$, $R^6$ is hydrogen, $R^4$ is a C1-C3 alkyl group optionally having one or more halogens, a C1-C3 alkoxy group optionally having one or more halogens, a C1-C3 alkylthio group optionally having one or more halogens, halogen, a hydroxyl group, a mercapto group, a nitro group, or a cyano group, and $R^5$ is hydrogen.

A pyrimidine compound of the formula (1) wherein $R^1$ is hydrogen, $R^2$ is hydrogen, $R^3$ is a C1-C3 alkyl group optionally having one or more halogens, a C1-C3 alkoxy group optionally having one or more halogens, a C1-C3 alkylthio group optionally having one or more halogens, a C1-C3 alkylsulfinyl group optionally having one or more halogens, a C1-C3 alkylsulfonyl group optionally having one or more halogens, hydrogen, or halogen, Z is oxygen, X is $=CR^6-$, $R^6$ is hydrogen, $R^4$ is a C1-C3 alkyl group optionally having one or more halogens, a C1-C3 alkoxy group optionally having one or more halogens, a C1-C3 alkylthio group optionally having one or more halogens, halogen, a hydroxyl group, a mercapto group, a nitro group, or a cyano group, and $R^5$ is hydrogen.

A pyrimidine compound of the formula (1) wherein $R^1$ is hydrogen, $R^2$ is hydrogen, $R^3$ is a C1-C3 alkyl group optionally having one or more halogens, a C1-C3 alkoxy group optionally having one or more halogens, a C1-C3 alkylthio group optionally having one or more halogens, a C1-C3 alkylsulfinyl group optionally having one or more halogens, a C1-C3 alkylsulfonyl group optionally having one or more halogens, hydrogen, or halogen, Z is $-NR^8-$, $R^8$ is a methyl group, X is $=CR^6-$, $R^6$ is hydrogen, $R^4$ is a C1-C3 alkyl group optionally having one or more halogens, a C1-C3 alkoxy group optionally having one or more halogens, a C1-C3 alkylthio group optionally having one or more halogens, halogen, a hydroxyl group, a mercapto group, a nitro group, or a cyano group, and $R^5$ is hydrogen.

A pyrimidine compound of the formula (1) wherein $R^1$ is hydrogen, $R^2$ is hydrogen, $R^3$ is a methyl group, an ethyl group, a propyl group, a trifluoromethyl group, a methoxy group, an ethoxy group, a propyloxy group, a trifluoromethoxy group, a 2,2-difluoroethoxy group, a 2,2,2-trifluoroethoxy group, a 2,2,4,4-tetrafluoropropoxy group, a methylthio group, an ethylthio group, a propylthio group, a trifluoromethylthio group, a 2,2,2-trifluoroethylthio group, a methylsulfinyl group, an ethylsulfinyl group, a propylsulfinyl group, a trifluoromethylsulfinyl group, a 2,2,2-trifluoroethylsulfinyl group, a methylsulfonyl group, an ethylsulfonyl group, a propylsulfonyl group, a trifluoromethylsulfonyl group, a 2,2,2-trifluoroethylsulfonyl group, hydrogen, fluorine, chlorine, or bromine, Z is oxygen or $-NR^8-$, $R^8$ is a methyl group, X is $=CR^6-$, $R^6$ is hydrogen, $R^4$ is a C1-C3 alkyl group optionally having one or more halogens, a C1-C3 alkoxy group optionally having one or more halogens, a C1-C3 alkylthio group optionally having one or more halogens, halogen, a hydroxyl group, a mercapto group, a nitro group, or a cyano group, and $R^5$ is hydrogen.

A pyrimidine compound of the formula (1) wherein $R^1$ is hydrogen, $R^2$ is hydrogen, $R^3$ is a C1-C3 alkyl group optionally having one or more halogens, a C1-C3 alkoxy group optionally having one or more halogens, a C1-C3 alkylthio group optionally having one or more halogens, a C1-C3 alkylsulfinyl group optionally having one or more halogens, a C1-C3 alkylsulfonyl group optionally having one or more halogens, hydrogen, or halogen, Z is oxygen or $-NR^8-$, $R^8$ is a methyl group, X is $=CR^6-$, $R^6$ is hydrogen, $R^4$ is a C1-C3 alkyl group having one or more fluorines, a C1-C3 alkoxy group having one or more fluorines, a C1-C3 alkylthio group having one or more fluorines, chlorine, or bromine, and $R^5$ is hydrogen.

A pyrimidine compound of the formula (1) wherein $R^1$ is hydrogen, $R^2$ is hydrogen, $R^3$ is a C1-C3 alkyl group optionally having one or more halogens, a C1-C3 alkoxy group optionally having one or more halogens, a C1-C3 alkylthio group optionally having one or more halogens, a C1-C3 alkylsulfinyl group optionally having one or more halogens, a C1-C3 alkylsulfonyl group optionally having one or more halogens, hydrogen, or halogen, Z is oxygen or $-NR^8-$, $R^8$ is a methyl group, X is $=CR^6-$, $R^6$ is hydrogen, $R^4$ is a trifluoromethyl group, a trifluoromethoxy group, a 2,2-difluoroethoxy group, a 2,2,2-trifluoroethoxy group, chlorine, or bromine, and $R^5$ is hydrogen.

A pyrimidine compound of the formula (1) wherein $R^1$ is hydrogen, $R^2$ is hydrogen, $R^3$ is a methyl group, an ethyl group, a propyl group, a trifluoromethyl group, a methoxy group, an ethoxy group, a propyloxy group, a trifluoromethoxy group, a 2,2-difluoroethoxy group, a 2,2,2-trifluoroethoxy group, a 2,2,4,4-tetrafluoropropoxy group, a methylthio group, an ethylthio group, a propylthio group, a trifluoromethylthio group, a 2,2,2-trifluoroethylthio group, a methylsulfinyl group, an ethylsulfinyl group, a propylsulfinyl group, a trifluoromethylsulfinyl group, a 2,2,2-trifluoroethylsulfinyl group, a methylsulfonyl group, an ethylsulfonyl group, a propylsulfonyl group, a trifluoromethylsulfonyl group, a 2,2,2-trifluoroethylsulfonyl group, hydrogen, fluorine, chlorine, or bromine, Z is oxygen or $-NR^8-$, $R^8$ is a methyl group, X is $=CR^6-$, $R^6$ is hydrogen, $R^4$ is a trifluoromethyl group, a trifluoromethoxy group, a 2,2-difluoroethoxy group, a 2,2,2-trifluoroethoxy group, chlorine, or bromine, and $R^5$ is hydrogen.

A pyrimidine compound of the formula (1) wherein $R^1$ is hydrogen, $R^2$ is hydrogen, $R^3$ is an ethyl group, a 2,2,2-trifluoroethoxy group, an ethylthio group, an ethylsulfinyl group, an ethylsulfonyl group, or chlorine, $R^4$ is a trifluoromethyl group, a pentafluoroethyl group, a trifluoromethylthio group, a trifluoromethylsulfinyl group, or a trifluoromethylsulfonyl group, and $R^5$ is hydrogen.

A pyrimidine compound of the formula (1) wherein $R^1$ is hydrogen, $R^2$ is hydrogen, $R^3$ is an ethyl group, a 2,2,2-trifluoroethoxy group, an ethylthio group, an ethylsulfinyl group, an ethylsulfonyl group, or chlorine, $R^4$ is a trifluoromethyl group, a pentafluoroethyl group, a trifluoromethylthio group, a trifluoromethylsulfinyl group, or a trifluoromethylsulfonyl group, $R^5$ is hydrogen, X is $=CR^6-$, $R^6$ is hydrogen, Y is $=CR^7-$, $R^7$ is hydrogen, Z is $-NR^8-$, and $R^8$ is a methyl group.

A pyrimidine compound of the formula (1) wherein $R^1$ is hydrogen, $R^2$ is hydrogen, $R^3$ is an ethyl group, a 2,2,2-trifluoroethoxy group, an ethylthio group, an ethylsulfinyl group, an ethylsulfonyl group, or chlorine, $R^4$ is a trifluoromethyl group, a pentafluoroethyl group, a trifluoromethylthio group, a trifluoromethylsulfinyl group, or a trifluoromethylsulfonyl group, $R^5$ is hydrogen, X is =$CR^6$—, $R^6$ is hydrogen, Y is nitrogen, Z is —$NR^8$—, and $R^8$ is a methyl group.

A pyrimidine compound of the formula (1) wherein $R^1$ is hydrogen, $R^2$ is hydrogen, $R^3$ is an ethyl group, a 2,2,2-trifluoroethoxy group, or chlorine, $R^4$ is a trifluoromethyl group, a pentafluoroethyl group, a trifluoromethylthio group, a trifluoromethylsulfinyl group, or a trifluoromethylsulfonyl group, $R^5$ is hydrogen, X is =$CR^6$—, $R^6$ is hydrogen, Y is nitrogen, Z is —$NR^8$—, and $R^8$ is a methyl group.

A pyrimidine compound of the formula (1) wherein $R^1$ is hydrogen, $R^2$ is hydrogen, $R^3$ is an ethyl group, an ethylsulfinyl group, an ethylsulfonyl group, or chlorine, $R^4$ is a trifluoromethyl group, a pentafluoroethyl group, a trifluoromethylthio group, a trifluoromethylsulfinyl group, or a trifluoromethylsulfonyl group, $R^5$ is hydrogen, X is =$CR^6$—, $R^6$ is hydrogen, Y is nitrogen, Z is —$NR^8$—, and $R^8$ is a methyl group.

The production method of the present compound is illustrated below.

The present compound can be produced, for example, according to the following Production methods A-G.

(Production Method A)

The present compound can be produced, for example, according to the following method:

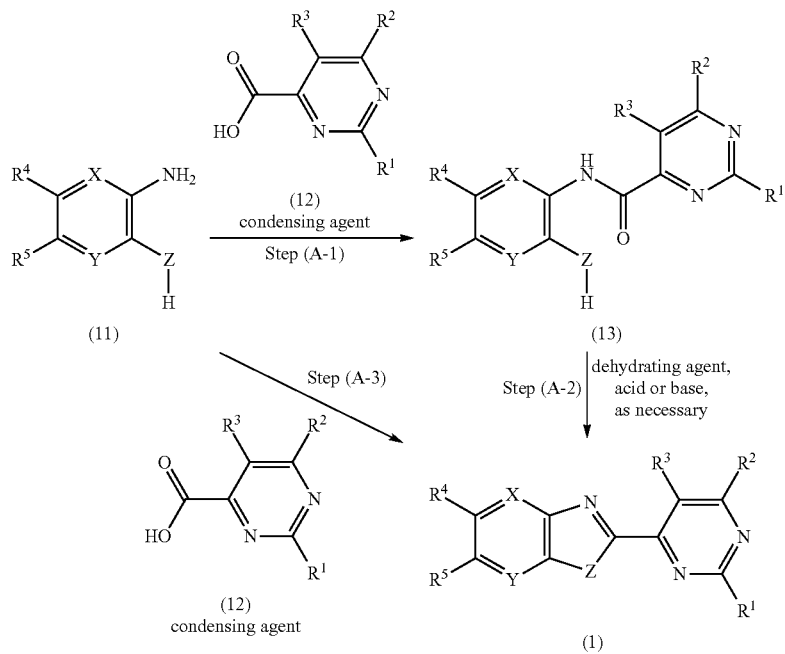

wherein $R^1$, $R^2$, $R^3$, $R^4$, $R^5$, X, Y, and Z are as defined above.

Step (A-1):

Compound (13) can be produced by reacting Compound (11) with Compound (12) in the presence of a condensing agent.

The reaction is performed in the presence or absence of a solvent. Examples of the solvent to be used in the reaction include ethers such as 1,4-dioxane, diethyl ether, tetrahydrofuran (hereinafter referred to as THF), and tert-butyl methyl ether; halogenated hydrocarbons such as dichloromethane, chloroform, carbon tetrachloride, 1,2-dichloroethane, and chlorobenzene; hydrocarbons such as toluene, benzene, and xylene; esters such as ethyl acetate and butyl acetate; nitriles such as acetonitrile; aprotic polar solvents such as N,N-dimethylformamide (hereinafter referred to as DMF), N-methylpyrrolidone (hereinafter referred to as NMP), 1,3-dimethyl-2-imidazolidinone, and dimethylsulfoxide; nitrogen-containing aromatic compounds such as pyridine and quinoline, and mixtures thereof.

Examples of the condensing agent to be used in the reaction include carbodiimides such as 1-ethyl-3-(3-dimethylaminopropyl)carbodiimide hydrochloride (hereinafter referred to as WSC) and 1,3-dicyclohexylcarbodiimide.

A catalyst can be added to the reaction as necessary.

Examples of the catalyst to be used in the reaction include 1-hydroxybenzotriazole.

The amount of Compound (12) to be used in the reaction is usually 1 to 2 moles based on 1 mole of Compound (11). The amount of the condensing agent to be used in the reaction is usually 1 to 5 moles based on 1 mole of Compound (11). The amount of the catalyst to be used in the reaction is usually 0.01 to 0.2 moles based on 1 mole of Compound (11).

The reaction temperature of the reaction is usually within a range of 0 to 100° C. The reaction time of the reaction is usually within a range of 0.1 to 24 hours.

After the completion of the reaction, Compound (13) can be isolated by adding the reaction mixture to water, extracting with an organic solvent, and concentrating the organic layer; adding the reaction mixture to water, and collecting the generated solids by filtration; or collecting the solids generated in the reaction mixture by filtration. The isolated Compound (13) can be further purified by recrystallization, chromatography, and the like.

Step (A-2)

The present compound can be produced by intramolecular-condensation of Compound (13).

The reaction is usually performed in the presence of a solvent. Examples of the solvent to be used in the reaction include ethers such as 1,4-dioxane, diethyl ether, THF, and tert-butyl methyl ether; halogenated hydrocarbons such as dichloromethane, chloroform, carbon tetrachloride, 1,2-dichloroethane, and chlorobenzene; hydrocarbons such as toluene, benzene, and xylene; esters such as ethyl acetate and butyl acetate; nitriles such as acetonitrile; aprotic polar solvents such as DMF, NMP, 1,3-dimethyl-2-imidazolidinone, and dimethylsulfoxide; nitrogen-containing aromatic compounds such as pyridine and quinoline; and mixtures thereof.

In the reaction, a dehydrating agent, acid or base can be used as necessary.

Examples of the dehydrating agent to be used in the reaction include phosphorous oxychloride, acetic anhydride, trifluoroacetic anhydride, a mixture of triphenylphosphine, base, and carbon tetrachloride or carbon tetrabromide, and a mixture of triphenylphosphine and azodiesters such as diethyl azodicarboxylate.

Examples of the acid to be used in the reaction include sulfonic acids such as para-toluenesulfonic acid, carboxylic acids such as acetic acid, and polyphosphoric acid.

Examples of the base to be used in the reaction include nitrogen-containing heterocyclic compounds such as pyridine, picoline, 2,6-lutidine, 1,8-diazabicyclo[5.4.0]-7-undecene (hereinafter referred to as DBU), and 1,5-diazabicyclo[4.3.0]-5-nonene; tertiary amines such as triethylamine and N-ethyldiisopropylamine; and inorganic bases such as potassium carbonate and sodium hydride.

The amount of the condensing agent to be used in the reaction is usually 1 to 5 moles based on 1 mole of Compound (13). The amount of the acid to be used in the reaction is 0.1 moles to 5 moles based on 1 mole of Compound (13). The amount of the base to be used in the reaction is 1 mole to 5 moles based on 1 mole of Compound (13).

The reaction temperature of the reaction is usually within a range of 0 to 200° C. The reaction time of the reaction is usually within a range of 0.1 to 24 hours.

After the completion of the reaction, the present compound can be isolated by adding the reaction mixture to water, extracting with an organic solvent, and concentrating the organic layer; adding the reaction mixture to water, and collecting the generated solids by filtration; or collecting the solids generated in the reaction mixture by filtration. The isolated present compound can be further purified by recrystallization, chromatography, and the like.

Step (A-3)

Also, the present compound can be produced by reacting Compound (11) with Compound (12).

The reaction is performed in the presence or absence of a solvent. Examples of the solvent to be used in the reaction include ethers such as 1,4-dioxane, diethyl ether, THF, and tert-butyl methyl ether; halogenated hydrocarbons such as dichloromethane, chloroform, carbon tetrachloride, 1,2-dichloroethane, and chlorobenzene; hydrocarbons such as toluene, benzene, and xylene; esters such as ethyl acetate and butyl acetate; nitriles such as acetonitrile; aprotic polar solvents such as DMF, NMP, 1,3-dimethyl-2-imidazolidinone, and dimethylsulfoxide; nitrogen-containing aromatic compounds such as pyridine and quinoline; and mixtures thereof.

Examples of the condensing agent to be used in the reaction include carbodiimides such as WSC and 1,3-dicyclohexyl-carbodiimide.

A catalyst can be added to the reaction as necessary.

Examples of the catalyst to be used in the reaction include 1-hydroxybenzotriazole.

The amount of Compound (12) to be used in the reaction is usually 1 to 2 moles based on 1 mole of Compound (11). The amount of the condensing agent to be used in the reaction is usually 1 to 5 moles based on 1 mole of Compound (11). The amount of the catalyst to be used in the reaction is usually 0.01 to 0.2 moles based on 1 mole of Compound (11).

The reaction temperature of the reaction is usually within a range of 0 to 200° C. The reaction time of the reaction is usually within a range of 0.1 to 24 hours.

After the completion of the reaction, the present compound can be isolated by adding the reaction mixture to water, extracting with an organic solvent, and concentrating the organic layer; adding the reaction mixture to water, and collecting the generated solids by filtration; or collecting the solids generated in the reaction mixture by filtration. The isolated present compound can be further purified by recrystallization, chromatography, and the like.

(Production Method B)

The present compound can be produced, for example, according to the following method.

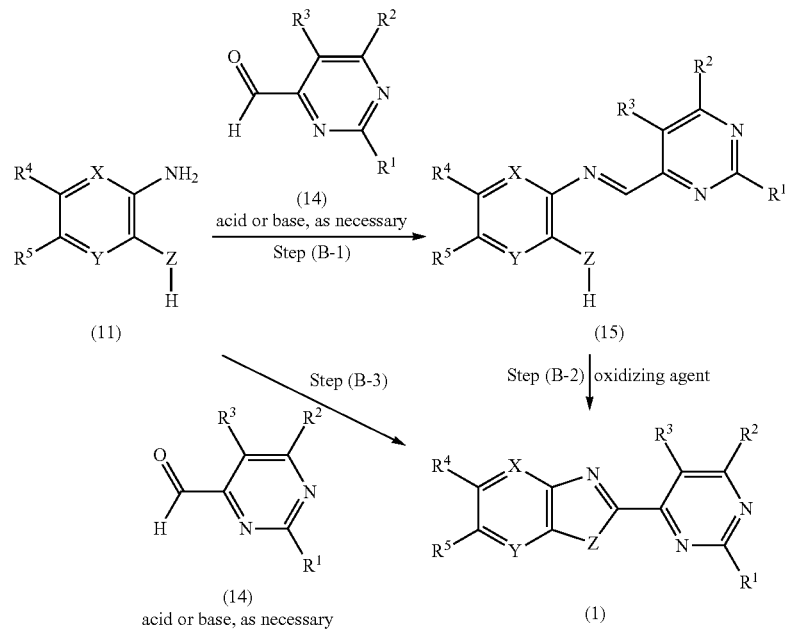

wherein $R^1$, $R^2$, $R^3$, $R^4$, $R^5$, X, Y, and Z are as defined above.

Step (B-1)

Compound (15) can be produced by reacting Compound (11) with Compound (14).

The reaction is usually performed in the presence of a solvent. Examples of the solvent to be used in the reaction include alcohols such as methanol and ethanol; ethers such as 1,4-dioxane, diethyl ether, THF, and tert-butyl methyl ether; halogenated hydrocarbons such as dichloromethane, chloroform, carbon tetrachloride, 1,2-dichloroethane, and chlorobenzene; hydrocarbons such as toluene, benzene, and xylene; esters such as ethyl acetate and butyl acetate; nitriles such as acetonitrile; aprotic polar solvents such as DMF, NMP, 1,3-dimethyl-2-imidazolidinone, and dimethylsulfoxide; nitrogen-containing aromatic compounds such as pyridine and quinoline; and mixtures thereof.

An acid or base can be added to the reaction as necessary.

The reaction temperature of the reaction is usually within a range of 0 to 150° C. The reaction time of the reaction is usually within a range of 0.1 to 24 hours.

After the completion of the reaction, Compound (15) can be isolated by adding the reaction mixture to water, extracting with an organic solvent, and concentrating the organic layer; adding the reaction mixture to water, and collecting the generated solids by filtration; or collecting the solids generated in the reaction mixture by filtration. The isolated Compound (15) can be further purified by recrystallization, chromatography, and the like.

Step (B-2)

The present compound can be produced by oxidizing Compound (15)

The reaction is usually performed in the presence of a solvent. Examples of the solvent to be used in the reaction include ethers such as 1,4-dioxane, diethyl ether, THF, and tert-butyl methyl ether; halogenated hydrocarbons such as dichloromethane, chloroform, carbon tetrachloride, 1,2-dichloroethane, and chlorobenzene; hydrocarbons such as toluene, benzene, and xylene; esters such as ethyl acetate and butyl acetate; nitriles such as acetonitrile; aprotic polar solvents such as DMF, NMP, 1,3-dimethyl-2-imidazolidinone, and dimethylsulfoxide; nitrogen-containing aromatic compounds such as pyridine and quinoline; and mixtures thereof.

Examples of the oxidizing agent to be used in the reaction include oxygen, metal oxidizing agents such as lead (IV) acetate and lead (IV) oxide, and organic periodides such as iodobenzene diacetate.

The reaction temperature of the reaction is usually within a range of 0 to 150° C. The reaction time of the reaction is usually within a range of 0.1 to 24 hours.

After the completion of the reaction, the present compound can be isolated by adding the reaction mixture to water, extracting with an organic solvent, and concentrating the organic layer; adding the reaction mixture to water, and collecting the generated solids by filtration; or collecting the solids generated in the reaction mixture by filtration. The isolated present compound can be further purified by recrystallization, chromatography, and the like.

Step (B-3)

Also, the present compound can be produced by reacting Compound (11) with Compound (14).

The reaction is usually performed in the presence of a solvent. Examples of the solvent to be used in the reaction include alcohols such as methanol and ethanol; ethers such as 1,4-dioxane, diethyl ether, THF, and tert-butyl methyl ether; halogenated hydrocarbons such as dichloromethane, chloroform, carbon tetrachloride, 1,2-dichloroethane, and chlorobenzene; hydrocarbons such as toluene, benzene, and xylene; esters such as ethyl acetate and butyl acetate; nitriles such as acetonitrile; aprotic polar solvents such as DMF, NMP, 1,3-dimethyl-2-imidazolidinone, and dimethylsulfoxide; nitrogen-containing aromatic compounds such as pyridine and quinoline; and mixtures thereof.

An acid or base can be added to the reaction as necessary.

The reaction temperature of the reaction is usually within a range of 0 to 200° C. The reaction time of the reaction is usually within a range of 0.1 to 24 hours.

After the completion of the reaction, the present compound can be isolated by adding the reaction mixture to water, extracting with an organic solvent, and concentrating the organic layer; adding the reaction mixture to water, and collecting the generated solids by filtration; or collecting the solids generated in the reaction mixture by filtration. The isolated present compound can be further purified by recrystallization, chromatography, and the like.

(Production Method C)

The present compound can be produced, for example, according to the following method.

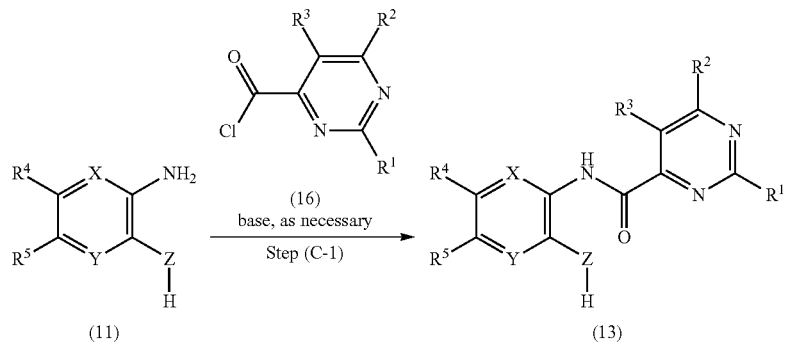

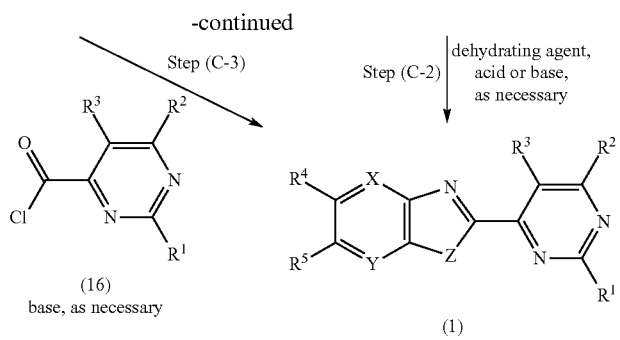

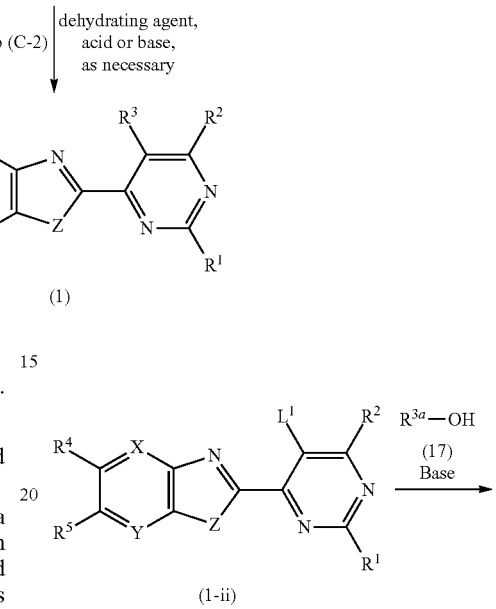

wherein $R^1$, $R^2$, $R^3$, $R^4$, $R^5$, X, Y, and Z are as defined above.

Step (C-1)

Compound (13) can be produced by reacting Compound (11) with Compound (16).

The reaction is performed in the presence or absence of a solvent. Examples of the solvent to be used in the reaction include ethers such as 1,4-dioxane, diethyl ether, THF, and tert-butyl methyl ether; halogenated hydrocarbons such as dichloromethane, chloroform, carbon tetrachloride, 1,2-dichloroethane, and chlorobenzene; hydrocarbons such as toluene, benzene, and xylene; esters such as ethyl acetate and butyl acetate; nitriles such as acetonitrile; aprotic polar solvents such as DMF, NMP, 1,3-dimethyl-2-imidazolidinone, and dimethylsulfoxide; nitrogen-containing aromatic compounds such as pyridine and quinoline; and mixtures thereof.

A base can be added to the reaction as necessary.

Examples of the base to be used in the reaction include nitrogen-containing heterocyclic compounds such as pyridine, picoline, 2,6-lutidine, DBU, and 1,5-diazabicyclo[4.3.0]-5-nonene; tertiary amines such as triethylamine and N-ethyldiisopropylamine; and inorganic bases such as potassium carbonate and sodium hydride.

The amount of Compound (16) to be used in the reaction is usually 1 to 2 moles based on 1 mole of Compound (11). The amount of the base to be used in the reaction is usually 1 to 5 moles based on 1 mole of Compound (11).

The reaction temperature of the reaction is usually within a range of 0 to 100° C. The reaction time of the reaction is usually within a range of 0.1 to 24 hours.

After the completion of the reaction, Compound (13) can be isolated by adding the reaction mixture to water, extracting with an organic solvent, and concentrating the organic layer; adding the reaction mixture to water, and collecting the generated solids by filtration; or collecting the solids generated in the reaction mixture by filtration. The isolated Compound (13) can be further purified by recrystallization, chromatography, and the like.

Step (C-2)

The present compound can be produced from Compound (13) by a similar method to Step (A-2) in Production method A.

Step (C-3)

The present compound can be produced by reacting Compound (11) with Compound (16) according to Step (C-1) in Production method C.

(Production Method D)

Among of the present compounds, the present compound (1-iii) wherein $R^3$ is $OR^{3a}$ can be produced by reacting Compound (1-ii) with Compound (17) in the presence of a base.

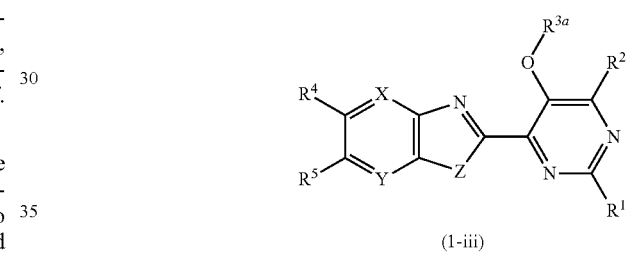

wherein $R^1$, $R^2$, $R^4$, $R^5$, X, Y, and Z are as defined above, $L^1$ is a leaving group such as chlorine, bromine, iodine, a para-toluenesulfonyloxy group, and a methanesulfonyloxy group, and $R^{3a}$ is a C1-C6 alkyl group optionally having one or more halogens.

The reaction is usually performed in the presence of a solvent, but a solvent amount of Compound (17) can be used.

Examples of the solvent to be used in the reaction include ethers such as 1,4-dioxane, diethyl ether, THF, and tert-butyl methyl ether; halogenated hydrocarbons such as dichloromethane, chloroform, carbon tetrachloride, 1,2-dichloroethane, and chlorobenzene; hydrocarbons such as toluene, benzene, and xylene; esters such as ethyl acetate and butyl acetate; nitriles such as acetonitrile; aprotic polar solvents such as DMF, NMP, 1,3-dimethyl-2-imidazolidinone, and dimethylsulfoxide; nitrogen-containing aromatic compounds such as pyridine and quinoline; and mixtures thereof.

Examples of the base to be used in the reaction include nitrogen-containing heterocyclic compounds such as pyridine, picoline, 2,6-lutidine, DBU, and 1,5-diazabicyclo[4.3.0]-5-nonene; tertiary amines such as triethylamine and N-ethyldiisopropylamine; and inorganic bases such as potassium carbonate and sodium hydride.

The amount of Compound (17) to be used in the reaction is usually 1 to 2 moles based on 1 mole of Compound (1-ii). The amount of the base to be used in the reaction is usually 1 to 5 moles based on 1 mole of Compound (1-ii).

The reaction temperature of the reaction is usually within a range of 0 to 100° C. The reaction time of the reaction is usually within a range of 0.1 to 24 hours.

After the completion of the reaction, the present compound (1-iii) can be isolated by adding the reaction mixture to water, extracting with an organic solvent, and concentrating the organic layer; adding the reaction mixture to water, and collecting the generated solids by filtration; or collecting the solids generated in the reaction mixture by filtration. The isolated the present compound (1-iii) can be further purified by recrystallization, chromatography, and the like.

(Production Method E)

Among of the present compounds, the present compound (1-iv) wherein $R^3$ is $SR^{3a}$ can be produced by reacting Compound (1-ii) with Compound (18) in the presence of a base.

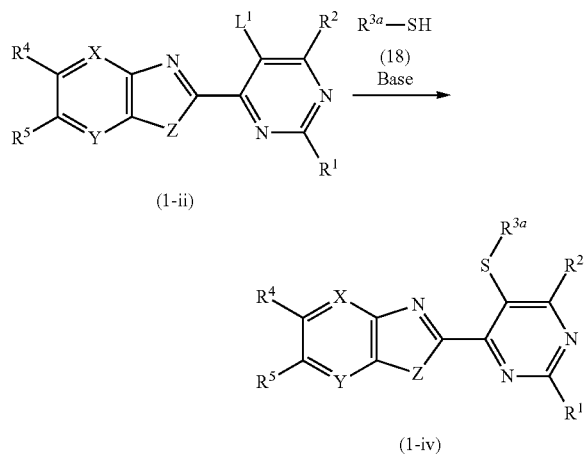

wherein $R^1$, $R^2$, $R^4$, $R^5$, $R^{3a}$, $L^1$, X, Y, and Z are as defined above.

The reaction is usually performed in the presence of a solvent. Examples of the solvent to be used in the reaction include ethers such as 1,4-dioxane, diethyl ether, THF, and tert-butyl methyl ether; halogenated hydrocarbons such as dichloromethane, chloroform, carbon tetrachloride, 1,2-dichloroethane, and chlorobenzene; hydrocarbons such as toluene, benzene, and xylene; esters such as ethyl acetate and butyl acetate; nitriles such as acetonitrile; aprotic polar solvents such as DMF, NMP, 1,3-dimethyl-2-imidazolidinone, and dimethylsulfoxide; nitrogen-containing aromatic compounds such as pyridine and quinoline; and mixtures thereof.

Examples of the base to be used in the reaction include nitrogen-containing heterocyclic compounds such as pyridine, picoline, 2,6-lutidine, DBU, and 1,5-diazabicyclo[4.3.0]-5-nonene; tertiary amines such as triethylamine and N-ethyldiisopropylamine; and inorganic bases such as potassium carbonate and sodium hydride.

The amount of Compound (18) to be used in the reaction is usually 1 to 2 moles based on 1 mole of Compound (1-ii). The amount of the base to be used in the reaction is usually 1 to 5 moles based on 1 mole of Compound (1-ii).

The reaction temperature of the reaction is usually within a range of 0 to 100° C. The reaction time of the reaction is usually within a range of 0.1 to 24 hours.

After the completion of the reaction, the present compound (1-iv) can be isolated by adding the reaction mixture to water, extracting with an organic solvent, and concentrating the organic layer; adding the reaction mixture to water, and collecting the generated solids by filtration; or collecting the solids generated in the reaction mixture by filtration. The isolated the present compound (1-iv) can be further purified by recrystallization, chromatography, and the like.

(Production Method F)

Among of the present compounds, the present compound (1-v) wherein $R^3$ is $NR^{3b}R^{3c}$ can be produced by Compound (1-ii) with Compound (19) in the presence of a base.

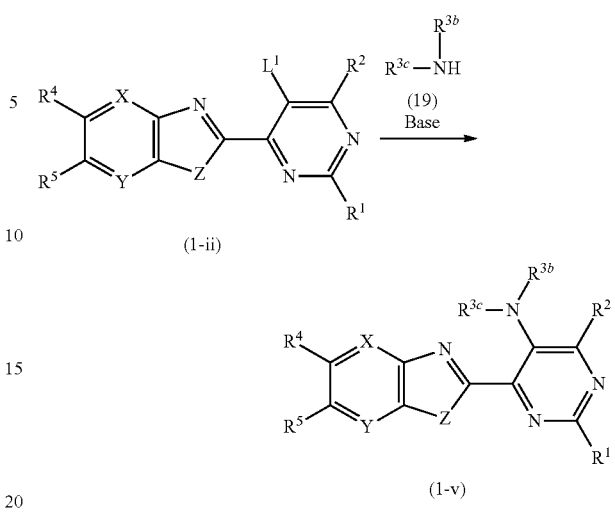

wherein $R^1$, $R^2$, $R^4$, $R^5$, $L^1$, X, Y, and Z are as defined above, $R^{3b}$ is a C1-C6 alkyl group optionally having one or more halogens, $R^{3c}$ is a C1-C6 alkyl group optionally having one or more halogens or hydrogen, provided that the total number of carbon atoms in $R^{3b}$ or $R^{3c}$ group is not more than 8.

The reaction is usually performed in the presence of a solvent, but a solvent amount of Compound (19) can be used.

Examples of the solvent to be used in the reaction include ethers such as 1,4-dioxane, diethyl ether, THF, and tert-butyl methyl ether; halogenated hydrocarbons such as dichloromethane, chloroform, carbon tetrachloride, 1,2-dichloroethane, and chlorobenzene; hydrocarbons such as toluene, benzene, and xylene; esters such as ethyl acetate and butyl acetate; nitriles such as acetonitrile; aprotic polar solvents such as DMF, NMP, 1,3-dimethyl-2-imidazolidinone, and dimethylsulfoxide; nitrogen-containing aromatic compounds such as pyridine and quinoline; and mixtures thereof.

Examples of the base to be used in the reaction include nitrogen-containing heterocyclic compounds such as pyridine, picoline, 2,6-lutidine, DBU, and 1,5-diazabicyclo[4.3.0]-5-nonene; tertiary amines such as triethylamine and N-ethyldiisopropylamine; and inorganic bases such as potassium carbonate and sodium hydride.

The amount of Compound (19) to be used in the reaction is usually 1 to 2 moles based on 1 mole of Compound (1-ii). The amount of the base to be used in the reaction is usually 1 to 5 moles based on 1 mole of Compound (1-ii).

The reaction temperature of the reaction is usually within a range of 0 to 100° C. The reaction time of the reaction is usually within a range of 0.1 to 24 hours.

After the completion of the reaction, the present compound (1-v) can be isolated by adding the reaction mixture to water, extracting with an organic solvent, and concentrating the organic layer; adding the reaction mixture to water, and collecting the generated solids by filtration; or collecting the solids generated in the reaction mixture by filtration. The isolated the present compound (1-v) can be further purified by recrystallization, chromatography, and the like.

(Production Method G)

Among of the present compounds, the present compound (1-vii) wherein $R^3$ is $R^{3d}$ can be produced by reacting the present compound (1-vi) with a boronic acid compound of Compound (20) or a tin compound of Compound (21) in the presence of a palladium compound and a base.

(1-vi) → (1-vii)

wherein $R^1$, $R^2$, $R^4$, $R^5$, X, Y, and Z are as defined above, $L^2$ is bromine or iodine, and $R^{3d}$ is a phenyl group optionally having one or more atoms or groups selected from Group α, or a 5-6 membered aromatic heterocyclic group optionally having one or more atoms or groups selected from Group α.

The reaction is usually performed in the presence of a solvent. Examples of the solvent to be used in the reaction include water, ethers such as 1,4-dioxane, diethyl ether, THF, and tert-butyl methyl ether; hydrocarbons such as toluene, benzene, and xylene; nitriles such as acetonitrile; aprotic polar solvents such as DMF, NMP, 1,3-dimethyl-2-imidazolidinone, and dimethylsulfoxide; and mixtures thereof.

Examples of the palladium compound to be used in the reaction include palladium-carbon, palladium chloride, palladium acetate, tetrakis(triphenylphosphine)palladium, {1,1'-bis(diphenylphosphino)ferrocene}dichloropalladium methylene chloride complex, and dichlorobis(triphenylphosphine)palladium (II).

Examples of the base to be used in the reaction include sodium hydroxide, sodium carbonate, potassium carbonate, cesium carbonate, sodium hydrogen carbonate, potassium acetate, and tripotassium phosphate.

The reaction can be performed in the presence of a phase transfer catalyst as necessary.

Examples of the phase transfer catalyst to be used in the reaction include quaternary ammonium salts such as tetrabutylammonium bromide and benzyltriethylammonium bromide.

The amount of Compound (20) or Compound (21) to be used in the reaction is usually 1 to 2 moles based on 1 mole of Compound (1-vi). The amount of the base to be used in the reaction is usually 1 to 5 moles based on 1 mole of Compound (1-vi).

The reaction temperature of the reaction is usually within a range of 0 to 100° C. The reaction time of the reaction is usually within a range of 0.1 to 24 hours.

After the completion of the reaction, the present compound (1-vii) can be isolated by adding the reaction mixture to water, extracting with an organic solvent, and concentrating the organic layer; adding the reaction mixture to water, and collecting the generated solids by filtration; or collecting the solids generated in the reaction mixture by filtration. The isolated the present compound (1-vii) can be further purified by recrystallization, chromatography, and the like.

The intermediates of the present invention can be produced, for example, by the following method.

(Reference Production Method 1)

Compound (11) can be produced, for example, by the following method.

(M1) → (M2) → (11)

wherein $R^4$, $R^5$, X, Y, and Z are as defined above.

(Step 1)

Compound (M2) can be produced by nitrating Compound (M1) in the presence of a nitrating agent.

The reaction is usually performed in the presence of a solvent.

Examples of the solvent to be used in the reaction include aliphatic halogenated hydrocarbons such as chloroform; acetic acid, concentrated sulfuric acid, concentrated nitric acid, water, and mixtures thereof.

Examples of the nitrating agent to be used in the reaction include concentrated nitric acid.

The amount of the nitrating agent is usually 1 to 3 moles based on 1 mole of Compound (M1).

The reaction temperature of the reaction is usually within a range of −10 to 100° C. The reaction time of the reaction is usually within a range of 0.1 to 24 hours.

After the completion of the reaction, Compound (M2) can be isolated by adding the reaction mixture to water, extracting with an organic solvent, and concentrating the organic layer; adding the reaction mixture to water, and collecting the generated solids by filtration; or collecting the solids generated in the reaction mixture by filtration. The isolated Compound (M2) can be further purified by recrystallization, chromatography, and the like.

(Step 2)

Compound (11) can be produced by reacting Compound (M2) with hydrogen in the presence of a hydrogenating catalyst.

The reaction is usually performed under 1 to 100 atoms of hydrogen, usually in the presence of a solvent.

Examples of the solvent to be used in the reaction include ethers such as THF and 1,4-dioxane; esters such as ethyl acetate and butyl acetate; alcohols such as methanol and ethanol, water, and mixtures thereof.

Examples of the hydrogenating catalyst to be used in the reaction include transition metal compounds such as palladium-carbon, palladium hydroxide, Raney® nickel, and platinum oxide.

The amount of hydrogen is usually 3 moles based on 1 mole of Compound (M2). The amount of the hydrogenation catalyst is usually 0.001 to 0.5 moles based on 1 mole of Compound (M2).

An acid or base can be added to the reaction as necessary.

The reaction temperature of the reaction is usually within a range of −20 to 100° C. The reaction time of the reaction is usually within a range of 0.1 to 24 hours.

After the completion of the reaction, Compound (11) can be isolated by adding the reaction mixture to water, extracting with an organic solvent, and concentrating the organic layer; adding the reaction mixture to water, and collecting the generated solids by filtration; or collecting the solids generated in the reaction mixture by filtration. The isolated Compound (11) can be further purified by recrystallization, chromatography, and the like.

(Reference Production Method 2)

Compound (12) can be produced, for example, by the following method.

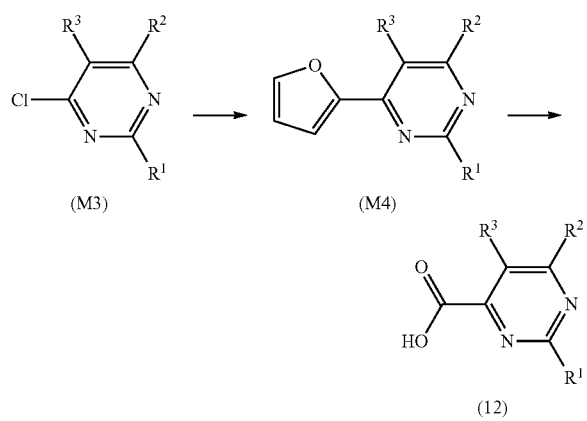

wherein $R^1$, $R^2$, and $R^3$ are as defined above.

(Step 1)

Compound (M4) can be produced by reacting Compound (M3) with 2-furylboronic acid in the presence of a palladium compound and a base.

The reaction is usually performed in the presence of a solvent. Examples of the solvent to be used in the reaction include water, ethers such as 1,4-dioxane, diethyl ether, THF, and tert-butyl methyl ether; hydrocarbons such as toluene, benzene, and xylene; nitriles such as acetonitrile; aprotic polar solvents such as DMF, NMP, 1,3-dimethyl-2-imidazolidinone, and dimethylsulfoxide; and mixtures thereof.

Examples of the palladium compound to be used in the reaction include palladium-carbon, palladium chloride, palladium acetate, tetrakis(triphenylphosphine)palladium, {1,1'-bis(diphenylphosphino)ferrocene}dichloropalladium methylene chloride complex, and dichlorobis(triphenylphosphine)palladium (II).

Examples of the base to be used in the reaction include sodium hydroxide, sodium carbonate, potassium carbonate, cesium carbonate, sodium hydrogen carbonate, potassium acetate, and tripotassium phosphate.

The reaction can be performed in the presence of a phase transfer catalyst as necessary.

Examples of the phase transfer catalyst to be used in the reaction include, for example, quaternary ammonium salts such as tetrabutylammonium bromide and benzyltriethylammonium bromide.

The amount of 2-furylboronic acid to be used in the reaction is usually 1 to 2 moles based on 1 mole of Compound (M3). The amount of the base to be used in the reaction is usually 1 to 5 moles based on 1 mole of Compound (M3).

The reaction temperature of the reaction is usually within a range of 0 to 100° C. The reaction time of the reaction is usually within a range of 0.1 to 24 hours.

After the completion of the reaction, Compound (M4) can be isolated by adding the reaction mixture to water, extracting with an organic solvent, and concentrating the organic layer; adding the reaction mixture to water, and collecting the generated solids by filtration; or collecting the solids generated in the reaction mixture by filtration. The isolated Compound (M4) can be further purified by recrystallization, chromatography, and the like.

(Step 2)

Compound (12) can be produced by reacting Compound (M4) with an oxidizing agent.

The reaction is usually performed in the presence of a solvent. Examples of the solvent to be used in the reaction include, for example, acetone, methyl isobutyl ketone, water, and mixtures thereof.

Examples of the oxidizing agent to be used in the reaction include potassium permanganate.

The amount of the oxidizing agent to be used in the reaction is usually 1 to 10 moles based on 1 mole of Compound (M4).

The reaction temperature of the reaction is usually within a range of −20 to 100° C. The reaction time of the reaction is usually within a range of 0.1 to 24 hours.

After the completion of the reaction, Compound (12) can be isolated by adding the reaction mixture to water, extracting with an organic solvent, and concentrating the organic layer; or adding the reaction mixture to water, and collecting the generated solids by filtration. The isolated Compound (12) can be further purified by recrystallization, chromatography, and the like.

Examples of the present compound are shown bellow.

A compound of the formula (A):

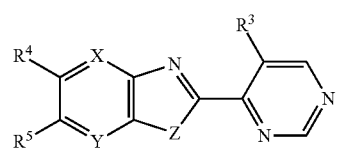

wherein Y is =CH—, Z is oxygen, and $R^3$, $R^4$, and $R^5$ represent a combination shown in Tables 1-11:

TABLE 1

| $R^3$ | $R^4$ | $R^5$ |
| --- | --- | --- |
| H | $CF_3$ | H |
| F | $CF_3$ | H |
| Cl | $CF_3$ | H |
| Br | $CF_3$ | H |
| I | $CF_3$ | H |
| $CH_3$ | $CF_3$ | H |
| $CH_2CH_3$ | $CF_3$ | H |
| $CH_2CH_2CH_3$ | $CF_3$ | H |
| $CH_2CH(CH_3)_2$ | $CF_3$ | H |
| $OCH_3$ | $CF_3$ | H |
| $OCH_2CH_3$ | $CF_3$ | H |
| $OCH_2CH_2CH_3$ | $CF_3$ | H |
| $OCH_2CH(CH_3)_2$ | $CF_3$ | H |
| $OCF_3$ | $CF_3$ | H |
| $OCH_2CF_3$ | $CF_3$ | H |
| $OCH_2CHF_2$ | $CF_3$ | H |
| $OCH_2CFH_2$ | $CF_3$ | H |
| $OCH_2CHFCHF_2$ | $CF_3$ | H |
| $OCH_2CF_2CHFCF_3$ | $CF_3$ | H |
| $SCH_3$ | $CF_3$ | H |

TABLE 2

| $R^3$ | $R^4$ | $R^5$ |
| --- | --- | --- |
| $SCH_2CH_3$ | $CF_3$ | H |
| $SCH_2CH_2CH_3$ | $CF_3$ | H |
| $SCH_2CH(CH_3)_2$ | $CF_3$ | H |
| $SCF_3$ | $CF_3$ | H |
| $SCH_2CF_3$ | $CF_3$ | H |
| $SCH_2CHF_2$ | $CF_3$ | H |
| $SCH_2CFH_2$ | $CF_3$ | H |
| $SCH_2CHFCHF_2$ | $CF_3$ | H |

TABLE 2-continued

| R³ | R⁴ | R⁵ |
|---|---|---|
| SCH₂CF₂CHFCF₃ | CF₃ | H |
| S(O)CH₃ | CF₃ | H |
| S(O)CH₂CH₃ | CF₃ | H |
| S(O)CH₂CH₂CH₃ | CF₃ | H |
| S(O)CH₂CH(CH₃)₂ | CF₃ | H |
| S(O)CF₃ | CF₃ | H |
| S(O)CH₂CF₃ | CF₃ | H |
| S(O)CH₂CHF₂ | CF₃ | H |
| S(O)CH₂CFH₂ | CF₃ | H |
| S(O)CH₂CHFCHF₂ | CF₃ | H |
| S(O)CH₂CF₂CHFCF₃ | CF₃ | H |
| S(O)₂CH₃ | CF₃ | H |

TABLE 3

| R³ | R⁴ | R⁵ |
|---|---|---|
| S(O)₂CH₂CH₃ | CF₃ | H |
| S(O)₂CH₂CH₂CH₃ | CF₃ | H |
| S(O)₂CH₂CH(CH₃)₂ | CF₃ | H |
| S(O)₂CF₃ | CF₃ | H |
| S(O)₂CH₂CF₃ | CF₃ | H |
| S(O)₂CH₂CHF₂ | CF₃ | H |
| S(O)₂CH₂CFH₂ | CF₃ | H |
| S(O)₂CH₂CHFCHF₂ | CF₃ | H |
| S(O)₂CH₂CF₂CHFCF₃ | CF₃ | H |
| NHCH₃ | CF₃ | H |
| NHCH₂CH₃ | CF₃ | H |
| NHCH₂CH₂CH₃ | CF₃ | H |
| NHCH(CH₃)₂ | CF₃ | H |
| N(CH₃)₂ | CF₃ | H |
| N(CH₂CH₃)₂ | CF₃ | H |
| NHC(O)CH₃ | CF₃ | H |
| NHC(O)OCH₃ | CF₃ | H |
| C(O)CH₃ | CF₃ | H |
| C(O)OCH₃ | CF₃ | H |
| CH₂OCH₃ | CF₃ | H |

TABLE 4

| R³ | R⁴ | R⁵ |
|---|---|---|
| CH₂OCH₂CH₃ | CF₃ | H |
| CH₂SCH₃ | CF₃ | H |
| CH₂SCH₂CH₃ | CF₃ | H |
| Phenyl | CF₃ | H |
| 2-SCH₃-phenyl | CF₃ | H |
| 2-SCH₂CH₃-phenyl | CF₃ | H |
| 1,2,4-triazol-1-yl | CF₃ | H |
| Pyrazol-1-yl | CF₃ | H |
| Pyridin-2-yl | CF₃ | H |
| Pyridin-3-yl | CF₃ | H |
| OH | CF3 | H |
| SH | CF3 | H |
| NH₂ | CF3 | H |
| CN | CF3 | H |
| NO₂ | CF3 | H |
| CHO | CF3 | H |

TABLE 5

| R³ | R⁴ | R⁵ |
|---|---|---|
| H | H | CF₃ |
| F | H | CF₃ |
| Cl | H | CF₃ |
| Br | H | CF₃ |
| CH₃ | H | CF₃ |
| CH₂CH₃ | H | CF₃ |
| OCH₃ | H | CF₃ |
| OCH₂CH₃ | H | CF₃ |

TABLE 5-continued

| R³ | R⁴ | R⁵ |
|---|---|---|
| OCH₂CF₃ | H | CF₃ |
| OCH₂CHF₂ | H | CF₃ |
| SCH₃ | H | CF₃ |
| SCH₂CH₃ | H | CF₃ |
| S(O)CH₃ | H | CF₃ |
| S(O)CH₂CH₃ | H | CF₃ |
| S(O)₂CH₃ | H | CF₃ |
| S(O)₂CH₂CH₃ | H | CF₃ |
| NHCH₂CH₃ | H | CF₃ |
| N(CH₂CH₃)₂ | H | CF₃ |

TABLE 6

| R³ | R⁴ | R⁵ |
|---|---|---|
| H | C(CH₃)₃ | H |
| F | C(CH₃)₃ | H |
| Cl | C(CH₃)₃ | H |
| Br | C(CH₃)₃ | H |
| CH₃ | C(CH₃)₃ | H |
| CH₂CH₃ | C(CH₃)₃ | H |
| OCH₃ | C(CH₃)₃ | H |
| OCH₂CH₃ | C(CH₃)₃ | H |
| OCH₂CF₃ | C(CH₃)₃ | H |
| OCH₂CHF₂ | C(CH₃)₃ | H |
| SCH₃ | C(CH₃)₃ | H |
| SCH₂CH₃ | C(CH₃)₃ | H |
| S(O)CH₃ | C(CH₃)₃ | H |
| S(O)CH₂CH₃ | C(CH₃)₃ | H |
| S(O)₂CH₃ | C(CH₃)₃ | H |
| S(O)₂CH₂CH₃ | C(CH₃)₃ | H |
| NHCH₂CH₃ | C(CH₃)₃ | H |
| N(CH₂CH₃)₂ | C(CH₃)₃ | H |

TABLE 7

| R³ | R⁴ | R⁵ |
|---|---|---|
| H | CHF₂ | H |
| F | CHF₂ | H |
| Cl | CHF₂ | H |
| Br | CHF₂ | H |
| CH₃ | CHF₂ | H |
| CH₂CH₃ | CHF₂ | H |
| OCH₃ | CHF₂ | H |
| OCH₂CH₃ | CHF₂ | H |
| OCH₂CF₃ | CHF₂ | H |
| OCH₂CHF₂ | CHF₂ | H |
| SCH₃ | CHF₂ | H |
| SCH₂CH₃ | CHF₂ | H |
| S(O)CH₃ | CHF₂ | H |
| S(O)CH₂CH₃ | CHF₂ | H |
| S(O)₂CH₃ | CHF₂ | H |
| S(O)₂CH₂CH₃ | CHF₂ | H |
| NHCH₂CH₃ | CHF₂ | H |
| N(CH₂CH₃)₂ | CHF₂ | H |

TABLE 8

| R³ | R⁴ | R⁵ |
|---|---|---|
| H | CF₂CF₃ | H |
| F | CF₂CF₃ | H |
| Cl | CF₂CF₃ | H |
| Br | CF₂CF₃ | H |
| CH₃ | CF₂CF₃ | H |
| CH₂CH₃ | CF₂CF₃ | H |
| OCH₃ | CF₂CF₃ | H |
| OCH₂CH₃ | CF₂CF₃ | H |
| OCH₂CF₃ | CF₂CF₃ | H |
| OCH₂CHF₂ | CF₂CF₃ | H |

TABLE 8-continued

| R³ | R⁴ | R⁵ |
|---|---|---|
| SCH₃ | CF₂CF₃ | H |
| SCH₂CH₃ | CF₂CF₃ | H |
| S(O)CH₃ | CF₂CF₃ | H |
| S(O)CH₂CH₃ | CF₂CF₃ | H |
| S(O)₂CH₃ | CF₂CF₃ | H |
| S(O)₂CH₂CH₃ | CF₂CF₃ | H |
| NHCH₂CH₃ | CF₂CF₃ | H |
| N(CH₂CH₃)₂ | CF₂CF₃ | H |

TABLE 9

| R³ | R⁴ | R⁵ |
|---|---|---|
| H | SCF₃ | H |
| F | SCF₃ | H |
| Cl | SCF₃ | H |
| Br | SCF₃ | H |
| CH₃ | SCF₃ | H |
| CH₂CH₃ | SCF₃ | H |
| OCH₃ | SCF₃ | H |
| OCH₂CH₃ | SCF₃ | H |
| OCH₂CF₃ | SCF₃ | H |
| OCH₂CHF₂ | SCF₃ | H |
| SCH₃ | SCF₃ | H |
| SCH₂CH₃ | SCF₃ | H |
| S(O)CH₃ | SCF₃ | H |
| S(O)CH₂CH₃ | SCF₃ | H |
| S(O)₂CH₃ | SCF₃ | H |
| S(O)₂CH₂CH₃ | SCF₃ | H |
| NHCH₂CH₃ | SCF₃ | H |
| N(CH₂CH₃)₂ | SCF₃ | H |

TABLE 10

| R³ | R⁴ | R⁵ |
|---|---|---|
| H | S(O)CF₃ | H |
| F | S(O)CF₃ | H |
| Cl | S(O)CF₃ | H |
| Br | S(O)CF₃ | H |
| CH₃ | S(O)CF₃ | H |
| CH₂CH₃ | S(O)CF₃ | H |
| OCH₃ | S(O)CF₃ | H |
| OCH₂CH₃ | S(O)CF₃ | H |
| OCH₂CF₃ | S(O)CF₃ | H |
| OCH₂CHF₂ | S(O)CF₃ | H |
| SCH₃ | S(O)CF₃ | H |
| SCH₂CH₃ | S(O)CF₃ | H |
| S(O)CH₃ | S(O)CF₃ | H |
| S(O)CH₂CH₃ | S(O)CF₃ | H |
| S(O)₂CH₃ | S(O)CF₃ | H |
| S(O)₂CH₂CH₃ | S(O)CF₃ | H |
| NHCH₂CH₃ | S(O)CF₃ | H |
| N(CH₂CH₃)₂ | S(O)CF₃ | H |

TABLE 11

| R³ | R⁴ | R⁵ |
|---|---|---|
| H | S(O)₂CF₃ | H |
| F | S(O)₂CF₃ | H |
| Cl | S(O)₂CF₃ | H |
| Br | S(O)₂CF₃ | H |
| CH₃ | S(O)₂CF₃ | H |
| CH₂CH₃ | S(O)₂CF₃ | H |
| OCH₃ | S(O)₂CF₃ | H |
| OCH₂CH₃ | S(O)₂CF₃ | H |
| OCH₂CF₃ | S(O)₂CF₃ | H |
| OCH₂CHF₂ | S(O)₂CF₃ | H |
| SCH₃ | S(O)₂CF₃ | H |
| SCH₂CH₃ | S(O)₂CF₃ | H |

TABLE 11-continued

| R³ | R⁴ | R⁵ |
|---|---|---|
| S(O)CH₃ | S(O)₂CF₃ | H |
| S(O)CH₂CH₃ | S(O)₂CF₃ | H |
| S(O)₂CH₃ | S(O)₂CF₃ | H |
| S(O)₂CH₂CH₃ | S(O)₂CF₃ | H |
| NHCH₂CH₃ | S(O)₂CF₃ | H |
| N(CH₂CH₃)₂ | S(O)₂CF₃ | H |

A compound of the formula (A) wherein Y is nitrogen, Z is oxygen, and $R^3$, $R^4$, and $R^5$ represent a combination shown in Tables 1-11.

A compound of the formula (A) wherein Y is =C(Cl)—, Z is oxygen, $R^3$, $R^4$, and $R^5$ represent a combination shown in Tables 1-11.

A compound of the formula (A) wherein Y is =CH—, Z is —N(CH₃)—, $R^3$, $R^4$, and $R^5$ represent a combination shown in Tables 1-11.

A compound of the formula (A) wherein Y is nitrogen, Z is —N(CH₃)—, $R^3$, $R^4$, and $R^5$ represent a combination shown in Tables 1-11.

A compound of the formula (A) wherein Y is =C(Cl)—, Z is —N(CH₃)—, $R^3$, $R^4$, and $R^5$ represent a combination shown in Tables 1-11.

Examples of pests against which the present compound has an activity include noxious arthropods such as noxious insects and noxious acarines, and nematodes. In particular, examples of the pests include the following.

Hemiptera: *Delphacidae* such as *Laodelphax striatellus*, *Nilaparvata lugens*, and *Sogatella furcifera*; *Deltocephalidae* such as *Nephotettix cincticeps*, *Nephotettix virescens*, and *Empoasca onukii*; *Aphididae* such as *Aphis gossypii*, *Myzus persicae*, *Brevicoryne brassicae*, *Aphis spiraecola*, *Macrosiphum euphorbiae*, *Aulacorthum solani*, *Rhopalosiphum padi*, *Toxoptera citricidus*, and *Hyalopterus pruni*; *Pentatomidae* such as *Nezara antennata*, *Riptortus clavetus*, *Leptocorisa chinensis*, *Eysarcoris parvus*, and *Halyomorpha mista*; *Aleyrodidae* such as *Trialeurodes vaporariorum*, *Bemisia tabaci*, *Dialeurodes citri*, and *Aleurocanthus spiniferus*; *Coccidae* such as *Aonidiella aurantii*, *Comstockaspis perniciosa*, *Unaspis citri*, *Ceroplastes rubens*, *Icerya purchasi*, *Planococcus kraunhiae*, *Pseudococcus longispinis*, and *Pseudaulacaspis pentagona*; *Tingidae*; *Cimices* such as *Cimex lectularius*; and *Psyllidae*.

Lepidoptera: *Pyralidae* such as *Chilo suppressalis*, *Tryporyza incertulas*, *Cnaphalocrocis medinalis*, *Notarcha derogata*, *Plodia interpunctella*, *Ostrinia furnacalis*, *Hellula undalis*, and *Pediasia teterrellus*; *Noctuidae* such as *Spodoptera litura*, *Spodoptera exigua*, *Pseudaletia separata*, *Mamestra brassicae*, *Agrotis ipsilon*, *Plusia nigrisigna*, *Thoricoplusia* spp., *Heliothis* spp., and *Helicoverpa* spp.; *Pieridae* such as *Pieris rapae*; *Tortricidae* such as *Adoxophyes* spp., *Grapholita molesta*, *Leguminivora glycinivorella*, *Matsumuraeses azukivora*, *Adoxophyes orana fasciata*, *Adoxophyes honmai.*, *Homona magnanima*, *Archips fuscocupreanus*, and *Cydia pomonella*; *Gracillariidae* such as *Caloptilia theivora* and *Phyllonorycter ringoneella*; *Carposimidae* such as *Carposina niponensis*; *Lyonetiidae* such as *Lyonetia* spp.; *Lymantriidae* such as *Lymantria* spp. and *Euproctis* spp; *Yponomeutidae* such as *Plutella xylostella*; *Gelechiidae* such as *Pectinophora gossypiella* and *Phthorimaea operculella*; *Arctiidae* such as *Hyphantria cunea*; and *Tineidae* such as *Tinea translucens* and *Tineola bisselliella*.

Thysanoptera: *Thripidae* such as *Frankliniella occidentalis*, *Thrips palmi*, *Scirtothrips dorsalis*, *Thrips tabaci*, and *Frankliniella intonsa*.

Diptera: *Culices* such as *Culex pipiens pallens*, *Culex tritaeniorhynchus*, and *Culex quinquefasciatus*; *Aedes* spp. such as *Aedes aegypti* and *Aedes albopictus*; *Anopheles* spp. such as *Anopheles sinensis*; *Chironomidae*; *Muscidae* such as

*Musca domestica* and *Muscina stabulans;* Calliphoridae; Sarcophagidae; Fanniidae; Anthomyiidae such as *Delia platura* and *Delia antiqua;* Agromyzidae such as *Agromyza oryzae, Hydrellia griseola, Liriomyza sativae, Liriomyza trifolii,* and *Chromatomyia horticol;* Chloropidae such as *Chlorops oryzae;* Tephritidae such as *Dacus cucurbitae* and *Ceratitis capitata;* Drosophilidae; Phoridae such as *Megaselia spiracularis;* Psychodidae such as *Clogmia albipunctata;* Simuliidae; Tabanidae such as *Tabanus trigonus*; and stable flies.

Coleoptera: *Diabrotica* spp. such as *Diabrotica virgifera virgifera* and *Diabrotica undecimpunctata howardi;* Scarabaeidae such as *Anomala cuprea, Anomala rufocuprea,* and *Popillia japonica*; weevils such as *Sitophilus zeamais, Lissorhoptrus oryzophilus, Callosobruchuys chienensis, Echinocnemus squameus, Anthonomus grandis,* and *Sphenophorus venatus; Tenebrionidae* such as *Tenebrio molitor* and *Tribolium castaneum;* Chrysomelidae such as *Oulema oryzae, Aulacophora femoralis, Phyllotreta striolata,* and *Leptinotarsa decemlineata;* Dermestidae such as *Anthrenus verbasci* and *Dermestes maculates;* Anobiidae such as *Lasioderma serricorne;* Epilachna such as *Epilachna vigintioctopunctata;* Scolytidae such as *Lyctus brunneus* and *Tomicus piniperda;* Bostrychidae; Ptinidae; Cerambycidae such as *Anoplophora malasiaca; Agriotes* spp., and *Paederus fuscipes.*

Orthoptera: *Locusta migratoria, Gryllotalpa africana, Oxya yezoensis, Oxya japonica,* and *Gryllidae.*

Hymenoptera: Formicidae such as *Monomorium pharaosis, Formica fusca japonica, Ochetellus glaber, Pristomyrmex pungens, Pheidole noda, Acromyrmex* spp., and *Solenopsis* spp.; Vespidae; Betylidae; and Tenthredinidae such as *Athalia rosae* and *Athalia japonica.*

Nematoda: *Aphelenchoides besseyi, Nothotylenchus acris, Meloidogyne incognita, Meloidogyne hapla, Meloidogyne javanica, Heterodera glycines, Globodera rostochiensis, Pratylenchus coffeae,* and *Pratylenchus neglectus.*

Blattodea: *Blattella germanica, Periplaneta fuliginosa, Periplaneta americana, Periplaneta brunnea,* and *Blatta orientalis.*

Acarina: Tetranychidae such as *Tetranychus urticae, Tetranychus kanzawai, Panonychus citri, Panonychus ulmi,* and *Oligonychus* spp.; Eriophyidae such as *Aculops pelekassi, Phyllocoptruta citri, Aculops lycopersici, Calacarus carinatus, Acaphylla theavagrans, Eriophyes chibaensis,* and *Aculus schlechtendali;* Tarsonemidae such as *Polyphagotarsonemus latus;* Tenuipalpidae such as *Brevipalpus phoenicis;* Tuckerellidae; Ixodidae such as *Haemaphysalis longicornis, Haemaphysalis flava, Dermacentor taiwanicus, Ixodes ovatus, Ixodes persulcatus, Ixodes scapularis, Boophilus microplus,* and *Rhipicephalus sanguineus;* Acaridae such as *Tyrophagus putrescentiae* and *Tyrophagus similis;* Pyroglyphidae such as *Dermatophagoides farinae* and *Dermatophagoides ptrenyssnus;* Cheyletidae such as *Cheyletus eruditus, Cheyletus malaccensis,* and *Cheyletus moorei;* Dermanyssidae such as *Ornithonyssus bacoti, Ornithonyssus sylvairum,* and *Dermanyssus gallinae;* Trombiculidae such as *Leptotrombidium akamushi*; and Araneae such as *Chiracanthium japonicum* and *Latrodectus hasseltii.*

The pest controlling agent of the present invention contains the present compound and an inert carrier. Generally, the pest controlling agent of the present invention is a formulation such as an emulsion, an oil solution, a powder, a granule, a wettable powder, a flowable formulation, a microcapsule, an aerosol, a smoking agent, a poison bait, and a resin formulation which are obtained by mixing the present compound and an inert carrier such as a solid carrier, a liquid carrier and a gaseous carrier, and further adding a surfactant and other adjuvant for formulation, if necessary.

The pest controlling agent of the present invention usually contains the present compound in an amount of 0.01% to 95% by weight.

Examples of the solid carrier to be used for formulation include a fine power and a granule of clays (such as kaolin clay, diatomite, bentonite, Fubasami clay, and acid clay), synthetic hydrated silicon oxide, talc, ceramic, other inorganic minerals (such as sericite, quartz, sulfur, activated carbon, calcium carbonate, and hydrated silica) or chemical fertilizers (such as ammonium sulfate, ammonium phosphate, ammonium nitrate, urea, and ammonium chloride).

Examples of the liquid carrier include water, alcohols (such as methanol, ethanol, isopropyl alcohol, butanol, hexanol, benzyl alcohol, ethylene glycol, propylene glycol, and phenoxyethanol), ketones (such as acetone, methyl ethyl ketone, and cyclohexanone), aromatic hydrocarbons (such as toluene, xylene, ethylbenzene, dodecylbenzene, phenylxylylethane, and methylnaphthalene), aliphatic hydrocarbons (such as hexane, cyclohexane, kerosine, and light oil), esters (such as ethyl acetate, butyl acetate, isopropyl mylistate, ethyl oleate, diisopropyl adipate, diisobutyl adipate, and propyleneglycol monomethyl ether acetate), nitriles (such as acetonitrile and isobutyronitrile), ethers (such as diisopropyl ether, 1,4-dioxane, ethylene glycol dimethyl ether, diethylene glycol dimethyl ether, diethylene glycol monomethyl ether, propylene glycol monomethyl ether, dipropylene glycol monomethyl ether, and 3-methoxy-3-methyl-1-butanol), acid amides (such as N,N-dimethylformamide and N,N-dimethylacetamide), halogenated hydrocarbons (such as dichloromethane, trichloroethane, and tetrachlorocarbon), sulfoxides (such as dimethylsulfoxide), propylene carbonate, and vegetable oils (such as soy bean oil and cotton seed oil).

Examples of the gaseous carrier include fluorocarbons, butane gas, liquefied petroleum gas (LPG), dimethyl ether, and carbon dioxide.

Examples of the surfactant include nonionic surfactant such as polyoxyethylene alkyl ether, polyoxyethylene alkylaryl ether, and polyethyleneglycol fatty acid ester; and anionic surfactant such as alkylsulfonic acid salts, alkylbenzenesulfonic acid salts and alkylsufic acid salts.

Examples of the other adjuvant for formulation include binders, dispersants, colorants and stabilizers, and particularly for example, casein, gelatin, polysaccharides (such as starch, gum arabic, cellulose derivatives, and alginic acid), lignin derivatives, synthetic water-soluble polymers (such as polyvinyl alcohol, polyvinylpyrrolidone, and polyacrylic acid), PAP (acidic isopropyl phosphate), BHT (2,6-di-t-butyl-4-methylphenol), and BHA (a mixture of 2-t-butyl-4-methoxyphenol and 3-t-butyl-4-methoxyphenol).

The method for controlling pests of the present invention is applying an effective amount of the present compound to pests directly and/or habitats of pests (such as plant, soil, indoor, and in-body of animals). The present compound is usually used as the pest controlling agent of the present invention in the method for controlling pests of the present invention.

When the pest controlling agent of the present invention is used for a control of pests in agriculture, the application amount is usually 1 to 10,000 g as the present compound per 10,000 $m^2$. When the pest controlling agent of the present invention is a formulation of emulsions, wettable powders or flowables, they are usually applied after a dilution with water to have an active ingredient concentration of 0.01 to 10,000 ppm. When the pest controlling agent of the present invention is a formulation of granules or powders, they are usually applied as such.

The formulations and the dilute aqueous solutions of the formulation may be sprayed directly to the plant to be protected from pests, or may be applied to the soil to control the pests living in a soil.

Furthermore, the resin formulations of sheets or strip form can be applied by a method such as winding around plants, stretching in the vicinity of plants, and laying on the soil surface at the plant bottom.

When the pest controlling agent of the present invention is used for a control of pests in indoor, the application amount is usually 0.01 to 1,000 mg as the present compound per 1 m² in case of application for plane surface, and 0.01 to 500 mg as the present compound per 1 m³ in case of application for space. When the pest controlling agent of the present invention is a formulation of emulsions, wettable powders or flowables, they are usually applied after a dilution with water to have an active ingredient concentration of 0.1 to 1,000 ppm. When the pest controlling agent of the present invention is a formulation of oil solutions, aerosols, smoking agents and poison baits, they are usually applied as such.

The pest controlling agent of the present invention could be used in farmlands on which "crops" shown below are cultivated.

Agricultural crops: corn, rice, wheat, barley, rye, oat, sorghum, cotton, soybean, peanut, sarrazin, sugar beet, rapeseed, sunflower, sugar cane, and tobacco;

Vegetables: Solanaceae vegetables (such as eggplant, tomato, green pepper, hot pepper, and potato), Cucurbitaceae vegetables (such as cucumber, pumpkin, zucchini, watermelon, and melon), Cruciferae vegetables (such as Japanese radish, turnip, horseradish, kohlrabi, Chinese cabbage, cabbage, brown mustard, broccoli, and cauliflower), Compositae vegetables (such as burdock, garland *chrysanthemum*, artichoke, and lettuce), Liliaceae vegetables (such as Welsh onion, onion, garlic, and asparagus), Umbelliferae vegetables (such as carrot, parsley, celery, and parsnip), Chenopodiaceae vegetables (such as spinach, and Swiss chard), Labiatae vegetables (such as Japanese basil, mint, and basil), strawberry, sweat potato, yam, and aroid;

Fruit trees: pomaceous fruits (such as apple, common pear, Japanese pear, Chinese quince, and quince), stone fleshy fruits (such as peach, plum, nectarine, Japanese plum, cherry, apricot, and prune), citrus plants (such as Satsuma mandarin, orange, lemon, lime, and grapefruit), nuts (such as chestnut, walnut, hazel nut, almond, pistachio, cashew nut, and macadamia nut), berry fruits (such as blueberry, cranberry, blackberry, and raspberry), grape, persimmon, olive, loquat, banana, coffee, date, coconut palm, and oil palm;

Trees other fruit trees: tea, mulberry, flowering trees (such as azalea, *japonica, hydrangea*, sasanqua, illicium anisatum, cherry tree, tulip poplar, crepe myetle, and orange osmanthus), street trees (such as ash tree, birch, dogwood, *eucalyptus*, ginkgo, lilac, maple tree, oak, poplar, *cercis*, Chinese sweet gum, plane tree, *zelkova*, Japanese arborvitae, fir tree, Japanese hemlock, needle juniper, pine, spruce, yew, elm, and horse-chestnut), sweet *viburnum, Podocarpus macrophyllus*, Japanese cedar, Japanese cypress, croton, spindle tree, and Chainese howthorn.

Lawn: *zoysia* (such as Japanese lawn grass and mascarene grass), Bermuda grass (such as *Cynodon dactylon*), bent grass (such as creeping bent grass, *Agrostis stolonifera*, and *Agrostis tenuis*), bluegrass (such as Kentucky bluegrass and rough bluegrass), fescue (such as tall fescue, chewing fescue, and creeping fescue), ryegrass (such as darnel and perennial ryegrass), cocksfoot, and timothy grass;

Others: flowers (such as rose, carnation, *chrysanthemum*, *Eustoma grandiflorum* Shinners, *gypsophila, gerbera*, pot marigold, *salvia, petunia, verbena*, tulip, aster, gentian, lily, pansy, cyclamen, orchid, lily of the valley, lavender, stock, ornamental kale, *primula*, poinsettia, *gladiolus*, cattleya, daisy, cymbidium, and *begonia*), biofuel plants (such as Jatropha curcas, safflower, *Camelina alyssum*, switchgrass, *miscanthus*, reed canary grass, *Arundo donax*, kenaf, cassava, willow, and algae), and foliage plant.

The "crops" include genetically modified crops.

The pest controlling agent of the present invention can be used as a mixture with or together with other insecticides, acaricides, nematocides, fungicides, plant growth regulators, herbicides, and synergists. Examples of active ingredients of the insecticide, the acaricide, the nematocide, the fungicide, the plant growth regulator, the herbicide, and the synergist are shown below.

Active Ingredients of Insecticides:

(1) Organic Phosphorus Compounds:

Acephate, Aluminium phosphide, butathiofos, cadusafos, chlorethoxyfos, chlorfenvinphos, chlorpyrifos, chlorpyrifos-methyl, cyanophos: CYAP, DCIP (diazinon, dichlorodiisopropyl ether), dichlofenthion: ECP, dichlorvos: DDVP, dimethoate, dimethylvinphos, disulfoton, EPN, ethion, ethoprophos, etrimfos, fenthion: MPP, fenitrothion: MEP, fosthiazate, formothion, Hydrogen phosphide, isofenphos, isoxathion, malathion, mesulfenfos, methidathion: DMTP, monocrotophos, naled: BRP, oxydeprofos: ESP, parathion, phosalone, phosmet: PMP, pirimiphos-methyl, pyridafenthion, quinalphos, phenthoate: PAP, profenofos, propaphos, prothiofos, pyraclorfos, salithion, sulprofos, tebupirimfos, temephos, tetrachlorvinphos, terbufos, thiometon, trichlorphon: DEP, vamidothion, phorate, and cadusafos.

(2) Carbamate Compounds:

Alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb: MIPC, metolcarb, methomyl, methiocarb, NAC, oxamyl, pirimicarb, propoxur: PHC, XMC, thiodicarb, xylylcarb, and aldicarb.

(3) Pyrethroid Compounds:

Acrinathrin, allethrin, benfluthrin, beta-cyfluthrin, bifenthrin, cycloprothrin, cyfluthrin, cyhalothrin, cypermethrin, deltamethrin, esfenvalerate, ethofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, tetramethrin, phenothrin, cyphenothrin, alpha-cypermethrin, zeta-cypermethrin, lambda-cyhalothrin, gamma-cyhalothrin, furamethrin, tau-fluvalinate, metofluthrin, profluthrin, dimefluthrin, 2,3,5,6-tetrafluoro-4-(methoxymethyl)benzyl (EZ)-(1RS,3RS;1RS, 3SR)-2,2-dimethyl-3-prop-1-enylcyclopropanecarboxylate, 2,3,5,6-tetrafluoro-4-methylbenzyl (EZ)-(1RS,3RS;1RS, 3SR)-2,2-dimethyl-3-prop-1-enylcyclopropanecarboxylate, and 2,3,5,6-tetrafluoro-4-(methoxymethyl)benzyl (1RS, 3RS;1RS,3SR)-2,2-dimethyl-3-(2-methyl-1-propenyl)cyclopropanecarboxylate.

(4) Nereistoxin Compounds:

Cartap, bensultap, thiocyclam, monosultap, and bisultap.

(5) Neonicotinoid Compounds:

Imidacloprid, nitenpyram, acetamiprid, thiamethoxam, thiacloprid, dinotefuran, and clothianidin.

(6) Benzoylurea Compounds:

Chlorfluazuron, bistrifluron, diafenthiuron, diflubenzuron, fluazuron, flucycloxuron, flufenoxuron, hexaflumuron, lufenuron, novaluron, noviflumuron, teflubenzuron, triflumuron, and triazuron.

(7) Phenylpyrazole Compounds:

Acetoprole, ethiprole, fipronil, vaniliprole, pyriprole, and pyrafluprole.

(8) Bt Toxines:

Live spores derived from and crystal toxins produced from *Bacillus* thuringiesis and a mixture thereof;

(9) Hydrazine Compounds:

Chromafenozide, halofenozide, methoxyfenozide, and tebufenozide.

(10) Organic Chlorine Compounds:

Aaldrin, dieldrin, dienochlor, endosulfan, and methoxychlor.

(11) Other Insecticidal Active Ingredients:

Machine oil, nicotine-sulfate; avermectin-B, bromopropylate, buprofezin, chlorphenapyr, cyantraniliprole, cyromazine, D-D (1,3-Dichloropropene), emamectin-benzoate, fenazaquin, flupyrazofos, hydroprene, methoprene, indoxacarb, metoxadiazone, milbemycin-A, pymetrozine, pyridalyl, pyriproxyfen, spinosad, sulfluramid, tolfenpyrad, triazamate, flubendiamide, lepimectin, arsenic acid, benclothiaz, calcium cyanamide, calcium polysulfide, chlordane, DDT, DSP, flufenerim, flonicamid, flurimfen, formetanate, metam-ammonium, metam-sodium, Methyl bromide, Potassium oleate, protrifenbute, spiromesifen, sulfoxaflor, sulfur, metaflumizone, spirotetramat, pyrifluquinazone, spinetoram, chlorantraniliprole, tralopyril, cyantraniliprole, a compound of the following formula (K):

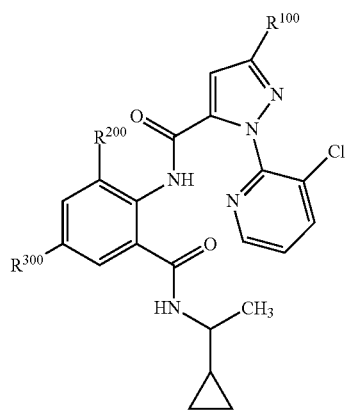

wherein:
$R^{100}$ is chlorine, bromine, or a trifluoromethyl group,
$R^{200}$ is chlorine, bromine, or a methyl group, and
$R^{300}$ is chlorine, bromine, or a cyano group,
and a compound of the following formula (L):

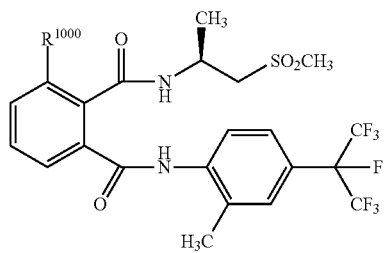

wherein:
$R^{1000}$ is chlorine, bromine, or iodine.

Active Ingredients of Acardides:
Acequinocyl, amitraz, benzoximate, bifenaate, bromopropylate, chinomethionat, chlorobenzilate, CPCBS (chlorfenson), clofentezine, cyflumetofen, Kelthane (dicofol), etoxazole, fenbutatin oxide, fenothiocarb, fenpyroximate, fluacrypyrim, fluproxyfen, hexythiazox, propargite: BPPS, polynactins, pyridaben, Pyrimidifen, tebufenpyrad, tetradifon, spirodiclofen, spiromesifen, spirotetramat, amidoflumet, and cyenopyrafen.

Active Ingredients of Nematocides:
DCIP, fosthiazate, levamisole hydrochloride (levamisole), methylsothiocyanate, morantel tartarate, and imicyafos.

Active Ingredients of Fungicides:
Azole fungicidal compounds such as propiconazole, prothioconazole, triadimenol, prochloraz, penconazole, tebuconazole, flusilazole, diniconazole, bromuconazole, epoxiconazole, difenoconazole, cyproconazole, metconazole, triflumizole, tetraconazole, myclobutanil, fenbuconazole, hexaconazole, fluquinconazole, triticonazole, bitertanol, imazalil, and flutriafol;

Cyclic amine fungicidal compounds such as fenpropimorph, tridemorph, and fenpropidin;

Benzimidazole fungicidal compounds such as carbendezim, benomyl, thiabendazole, and thiophanate-methyl;

Procymidone; cyprodinil; pyrimethanil; diethofencarb; thiuram; fluazinam; mancozeb; iprodione; vinclozolin; chlorothalonil; captan; mepanipyrim; fenpiclonil; fludioxonil; dichlofluanid; folpet; kresoxim-methyl; azoxystrobin; trifloxystrobin; fluoxastrobin; picoxystrobin; pyraclostrobin; dimoxystrobin; pyribencarb; spiroxamine; quinoxyfen; fenhexamid; famoxadone; fenamidone; zoxamide; ethaboxam; amisulbrom; iprovalicarb; benthiavalicarb; cyazofamid; mandipropamid; boscalid; penthiopyrad; metrafenone; fluopiran; bixafen; cyflufenamid; proquinazid; isotianil, and tiadinil.

Active Ingredients of Herbicides:
(1) Phenoxyfatty Acid Herbicidal Compounds:
2,4-PA, MCP, MCPB, phenothiol, mecoprop, fluoroxypyr, triclopyr, clomeprop, and naproanilide.
(2) Benzoic Acid Herbicidal Compounds:
2,3,6-TBA, dicamba, clopyralid, picloram, aminopyralid, quinclorac, and quinmerac.
(3) Urea Herbicidal Compounds:
Diuron, linuron, chlortoluron, isoproturon, fluometuron, isouron, tebuthiuron, methabenzthiazuron, cumyluron, daimuron, and methyl-daimuron.
(4) Triazine Herbicidal Compounds:
Atrazine, ametoryn, cyanazine, simazine, propazine, simetryn, dimethametryn, prometryn, metribuzin, triaziflam, and indaziflam.
(5) Bipyridinium Herbicidal Compounds:
Paraquat and diquat.
(6) Hydroxybenzonitrile Herbicidal Compounds:
Bromoxynil and ioxynil.
(7) Dinitroaniline Herbicidal Compounds:
Pendimethalin, prodiamine, and trifluralin.
(8) Organic Phosphorus Herbicidal Compounds:
Amiprofos-methyl, butamifos, bensulide, piperophos, anilofos, glyphosate, glufosinate, glufosinate-P, and bialaphos.
(9) Carbamate Herbicidal Compounds:
Di-allate, tri-allate, EPTC, butylate, benthiocarb, esprocarb, molinate, dimepiperate, swep, chlorpropham, phenmedipham, phenisopham, pyributicarb, and asulam.
(10) Acid Amide Herbicidal Compounds:
Propanil, propyzamide, bromobutide, and etobenzanid.
(11) Chloroacetanilide Herbicidal Compounds:
Acetochlor, alachlor, butachlor, dimethenamid, propachlor, metazachlor, metolachlor, pretilachlor, thenylchlor, and pethoxamid.
(12) Diphenylether Herbicidal Compounds:
Acifluorfen-sodium, bifenox, oxyfluorfen, lactofen, fomesafen, chlomethoxynil, and aclonifen.
(13) Cyclic Imide Herbicidal Compounds:
Oxadiazon, cinidon-ethyl, carfentrazone-ethyl, surfentrazone, flumiclorac-pentyl, flumioxazin, pyraflufen-ethyl, oxadiargyl, pentoxazone, fluthiacet-methyl, butafenacil, benzfendizone, bencarbazone, and saflufenacil.
(14) Pyrazole Herbicidal Compounds:
Benzofenap, pyrazolate, pyrazoxyfen, topramezone, and pyrasulfotole.
(15) Triketone Herbicidal Compounds:
Isoxaflutole, benzobicyclon, sulcotrione, mesotrione, tembotrione, and tefuryltrione.
(16) Aryloxyphenoxypropionic Acid Herbicidal Compounds:
Clodinafop-propargyl, cyhalofop-butyl, diclofop-methyl, fenoxaprop-ethyl, fluazifop-butyl, haloxyfop-methyl, quizalofop-ethyl, and metamifop.

(17) Trioneoxime Herbicidal Compounds:
Alloxydim-sodium, sethoxydim, butroxydim, clethodim, cloproxydim, cycloxydim, tepraloxydim, tralkoxydim, and profoxydim.
(18) Sulfonylurea Herbicidal Compounds:
Chlorsulfuron, sulfometuron-methyl, metsulfuron-methyl, chlorimuron-ethyl, tribenuron-methyl, triasulfuron, bensulfuron-methyl, thifensulfuron-methyl, pyrazosulfuron-ethyl, primisulfuron-methyl, nicosulfuron, amidosulfuron, cinosulfuron, imazosulfuron, rimsulfuron, halosulfuron-methyl, prosulfuron, ethametsulfuron-methyl, triflusulfuron-methyl, flazasulfuron, cyclosulfamuron, flupyrsulfuron, sulfosulfuron, azimsulfuron, ethoxysulfuron, oxasulfuron, iodosulfuron-methyl-sodium, foramsulfuron, mesosulfuron-methyl, trifloxysulfuron, tritosulfuron, orthosulfamuron, flucetosulfuron, and propyrisulfuron.
(19) Imidazolinone Herbicidal Compounds:
Imazamethabenz-methyl, imazamethapyr, imazamox, imazapyr, imazaquin, and imazethapyr.
(20) Sulfonamide Herbicidal Compounds:
Flumetsulam, metosulam, diclosulam, florasulam, cloransulam-methyl, penoxsulam, and pyroxsulam.
(21) Pyrimidinyloxybenzoic Acid Herbicidal Compounds:
Pyrithiobac-sodium, bispyribac-sodium, pyriminobac-methyl, pyribenzoxim, pyriftalid, and pyrimisulfan.
(22) Other Herbicidal Compounds:
Bentazon, bromacil, terbacil, chlorthiamid, isoxaben, dinoseb, amitrole, cinmethylin, tridiphane, dalapon, diflufenzopyr-sodium, dithiopyr, thiazopyr, flucarbazone-sodium, propoxycarbazone-sodium, mefenacet, flufenacet, fentrazamide, cafenstrole, indanofan, oxaziclomefone, benfuresate, ACN, pyridate, chloridazon, norflurazon, flurtamone, diflufenican, picolinafen, beflubutamid, clomazone, amicarbazone, pinoxaden, pyraclonil, pyroxasulfone, thiencarbazone-methyl, aminocyclopyrachlor, ipfencarbazone, and methiozolin.

Active Ingredients of Synergists:
Piperonyl butoxide, sesamex, sulfoxide, N-(2-ethylhexyl)-8,9,10-trinorborn-5-ene-2,3-dicarboxylmide (MGK 264), N-declyimidazole, WARF-antiresistant, TBPT, TPP, IBP, PSCP, methyl iodide ($CH_3I$), t-phenylbutenone, diethylmaleate, DMC, FDMC, ETP, and ETN.

EXAMPLES

The present invention is described in more detail by Production Examples, Formulation Examples, and Test Examples, but the present invention is not limited to these Examples.

First, Production Examples of the present compound are shown below.

Production Example 1

A mixture of $N^1$-methyl-4-trifluoromethyl-benzene-1,2-diamine (1.14 g), 5-chloro-pyrimidine-4-carboxylic acid (1.14 g), WSC (1.02 g), and pyridine (12 ml) was stirred at 115° C. for 3 hours. After standing to cool to room temperature, to the reaction mixture, water was added, and extracted with ethyl acetate. The organic layer was dried over magnesium sulfate, and concentrated under reduced pressure. To the resulting residue, para-toluenesulfonic acid monohydrate (3.42 g) and xylene (12 ml) were added, and the reaction mixture was stirred at 140° C. for 3 hours with removing water using a Dean-Stark apparatus. After standing to cool the reaction mixture to room temperature, to the reaction mixture, water was added, and extracted with ethyl acetate. The organic layer was dried over magnesium sulfate, and concentrated under reduced pressure. The residue was subjected to silica gel column chromatography to give 0.40 g of the compound of the formula:

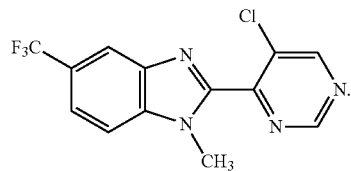

(Compound 14)

Production Example 2

To a mixture of sodium ethyl mercaptanate (0.16 g) and DMF (4 ml), 2-(5-chloropyrimidin-4-yl)-1-methyl-5-trifluoromethyl-1H-benzimidazole (Compound 14) (0.40 g) was added under ice-cooling, and the reaction mixture was stirred at room temperature for 1 hour. To the reaction mixture, saturated aqueous sodium hydrogen carbonate solution was added, and extracted with ethyl acetate. The organic layer was dried over magnesium sulfate, and concentrated under reduced pressure. The residue was subjected to silica gel column chromatography to give 0.39 g of the compound of the formula:

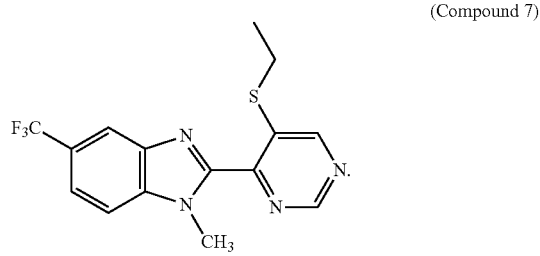

(Compound 7)

Production Example 3

To a mixture of 2-(5-ethylthiopyrimidin-4-yl)-1-methyl-5-trifluoromethyl-1H-benzimidazole (Compound 7) (0.29 g) and chloroform (4 ml), 69-75% of 3-chloroperbenzoic acid (0.28 g) was added under ice-cooling. After stirring the reaction mixture at room temperature for 0.5 hours, a saturated aqueous sodium hydrogen carbonate solution and a saturated aqueous sodium thiosulfate solution were added, and the reaction mixture was extracted with chloroform. The organic layer was dried over magnesium sulfate, and concentrated under reduced pressure. The residue was subjected to silica gel column chromatography to give 0.18 g of the compound of the formula:

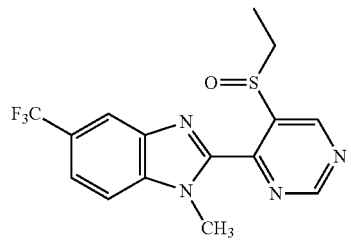

(Compound 8)

and 0.11 g of the compound of the formula:

(Compound 9)

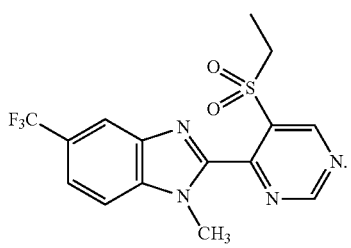

Production Example 4

A mixture of 4,6-dichloro-5-ethylpyrimidine (10 g), 2-furylboronic acid (6.33 g) tetrakis(triphenylphosphine)palladium (1.94 g), dimethoxyethane (100 ml), and sodium carbonate solution (2 mol/l) (60 ml) was stirred at 70° C. for 2 hours and at 80° C. for 2 hours. After standing to cool the reaction mixture to room temperature, to the reaction mixture, water was added, and extracted with ethyl acetate. The organic layer was dried over sodium sulfate, and concentrated under reduced pressure. The residue was subjected to silica gel column chromatography to give 6.06 g of 4-chloro-5-ethyl-6-(furan-2-yl)-pyrimidine.

4-chloro-5-ethyl-6-(furan-2-yl)-pyrimidine

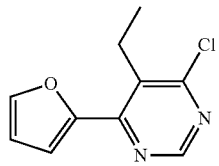

$^1$H-NMR (CDCl$_3$) δ: 1.31 (3H, t), 3.14 (2H, q), 6.62 (1H, dd), 7.33 (1H, dd), 7.68 (1H, dd), 8.76 (1H, s).

A mixture of 4-chloro-5-ethyl-6-(furan-2-yl)-pyrimidine (3.0 g), hydrazine monohydrate (3.0 g), triethylamine (3.0 g), and THF (20 ml) was stirred under reflux for 2 hours. To the mixture, hydrazine monohydrate (1 g) was added, and stirred under reflux for 3 hours. After standing to cool the reaction mixture to room temperature, to the reaction mixture, water was added, and extracted with ethyl acetate. The organic layer was dried over sodium sulfate, and concentrated under reduced pressure to give 2.85 g of [5-ethyl-6-(furan-2-yl)-pyrimidin-4-yl]-hydrazine.

[5-ethyl-6-(furan-2-yl)-pyrimidin-4-yl]-hydrazine

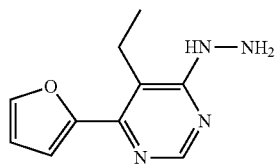

$^1$H-NMR (CDCl$_3$) δ: 1.26 (3H, t), 2.77 (2H, q), 4.09 (2H, brs), 6.22 (1H, brs), 6.56 (1H, dd), 7.11 (1H, dd), 7.60 (1H, dd), 8.58 (1H, s).

To a mixture of [5-ethyl-6-(furan-2-yl)-pyrimidin-4-yl]-hydrazine (2.85 g), acetonitrile (50 ml), and para-toluensulfonyl chloride (2.86 g), pyridine (2.37 g) was added under ice-cooling, and the reaction mixture was stirred at room temperature for 2 hours. To the reaction mixture, water (50 ml) was added, and the precipitated solids were collected by filtration. The solid was sequentially washed with water (20 ml) and acetonitrile (20 ml), and dried. To the resulting solid, sodium hydroxide (8.1 g), ethylene glycol (100 ml), and water (50 ml) were added, and stirred under reflux for 3 hours. After standing to cool the reaction mixture to room temperature, to the reaction mixture, water was added, and extracted with ethyl acetate. The organic layer was dried over sodium sulfate, and concentrated under reduced pressure. The residue was subjected to silica gel column chromatography to give 2.03 g of 5-ethyl-4-furan-2-yl-pyrimidine.

5-ethyl-4-(furan-2-yl)-pyrimidine

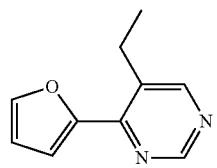

$^1$H-NMR (CDCl$_3$) δ: 1.31 (3H, t), 2.99 (2H, q), 6.61 (1H, dd), 7.29 (1H, dd), 7.67 (1H, dd), 8.59 (1H, s), 9.04 (1H, s).

A mixture of 5-ethyl-4-(furan-2-yl)-pyrimidine (2.03 g), acetone (70 ml), and water (35 ml) was stirred at 50° C., potassium permanganate (15 g) was added thereto over 15 minutes, and the reaction mixture was stirred under reflux for 1 hour. After standing to cool the reaction mixture to room temperature, to the reaction mixture, saturated aqueous sodium hydrogen carbonate solution was added, and extracted with tert-butyl methyl ether. To the resulting aqueous layer, hydrochloric acid was added, and extracted with tert-butyl methyl ether. The organic layer was dried over sodium sulfate, and concentrated under reduced pressure to give 1.14 g of 5-ethyl-pyrimidine-4-carboxylic acid.

5-ethyl-pyrimidine-4-carboxylic acid

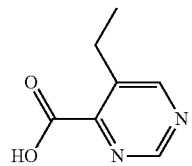

$^1$H-NMR (CDCl$_3$) δ: 1.33 (3H, t), 3.22 (2H, q), 8.90 (1H, s), 9.18 (1H, s).

To a mixture of 3-amino-5-trifluoromethylpyridin-2-ol (0.27 g), WSC (0.58 g), and pyridine (10 ml), 5-ethyl-pyrimidine-4-carboxylic acid was added under ice-cooling, and the reaction mixture was stirred at 80° C. for 10 hours. After standing to cool the reaction mixture to room temperature, to the reaction mixture, saturated aqueous sodium hydrogen carbonate solution was added, and extracted with ethyl acetate. The organic layer was dried over sodium sulfate, and concentrated under reduced pressure. The residue was subjected to silica gel column chromatography to give 0.26 g of 5-ethyl-N-(2-hydroxy-5-trifluoromethyl-pyridin-3-yl)-pyrimidine-4-carboxamide.

5-ethyl-N-(2-hydroxy-5-trifluoromethyl-pyridin-3-yl)-pyrimidine-4-carboxamide

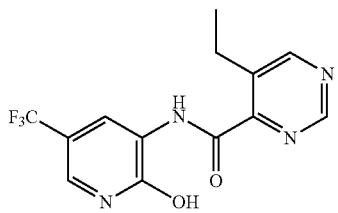 [SMILES: CCc1cncnc1C(=O)Nc1cc(C(F)(F)F)cnc1O]

To a mixture of 5-ethyl-N-(2-hydroxy-5-trifluoromethyl-pyridin-3-yl)-pyrimidine-4-carboxamide (0.26 g), triphenylphosphine (0.24 g), and THF (20 ml), diethyl azodicarboxylate (40% of toluene solution) (0.41 ml) was added under ice-cooling, and the reaction mixture was stirred at 50° C. for 10 hours. After standing to cool the reaction mixture to room temperature, to the reaction mixture, water was added, and extracted with ethyl acetate. The organic layer was dried over sodium sulfate, and concentrated under reduced pressure. The residue was subjected to silica gel chromatography to give 0.19 g of the formula:

(Compound 15)

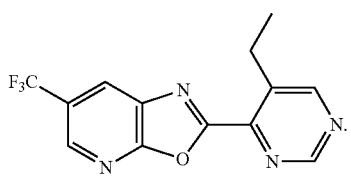

Production Example 5

A mixture of $N^1$-methyl-4-trifluoromethyl-benzene-1,2-diamine (0.29 g), pyrimidine-4-carbaldehyde (0.20 g), sodium sulfite (0.48 g), and DMF (8 ml) was stirred at 80° C. for 2 hours, then at 100° C. for 2.5 hours. After standing to cool the reaction mixture to room temperature, to the reaction mixture, saturated aqueous ammonium chloride solution was added, and extracted with ethyl acetate. The organic layer was dried over magnesium sulfate, and concentrated under reduced pressure. The residue was subjected to silica gel column chromatography to give 0.20 g of the compound of the formula:

(Compound 2)

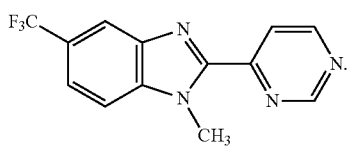

Production Example 6

To a mixture of $N^2$-methyl-5-trifluoromethylpyridine-2,3-diamine (2.65 g), WSC (2.66 g), 4-dimethylaminopyridine (0.10 g), THF (10 ml), and pyridine (10 ml), 5-chloropyrimidine-4-carboxylic acid was added under ice-cooling, and the reaction mixture was stirred at 50° C. for 8 hours. After standing to cool the reaction mixture to room temperature, to the reaction mixture, saturated aqueous sodium hydrogen carbonate solution was added, and extracted with ethyl acetate. The organic layer was dried over sodium sulfate, and concentrated under reduced pressure. The residue was subjected to silica gel column chromatography to give 1.77 g of 5-chloro-N-(2-methylamino-5-trifluoromethyl-pyridin-3-yl)-pyrimidine-4-carboxamide.

5-chloro-N-(2-methylamino-5-trifluoromethyl-pyridin-3-yl)-pyrimidine-4-carboxamide

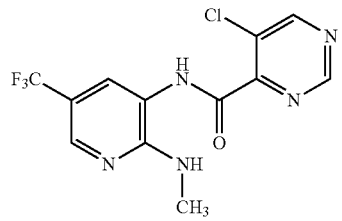 [SMILES: CNc1ncc(C(F)(F)F)cc1NC(=O)c1ncncc1Cl]

$^1$H-NMR (CDCl$_3$) δ: 9.47-9.39 (1H, m), 9.19 (1H, s), 9.00 (1H, s), 8.39 (1H, s), 7.89 (1H, s), 5.02-4.88 (1H, m), 3.10 (3H, d).

To a mixture of 5-chloro-N-(2-methylamino-5-trifluoromethyl-pyridin-3-yl)-pyrimidine-4-carboxamide (1.77 g) and xylene (100 ml), para-toluenesulfonic acid monohydrate (2.23 g) was added at room temperature, and the reaction mixture was stirred at 170° C. for 2 days. After standing to cool the reaction mixture to room temperature, to the reaction mixture, saturated aqueous sodium hydrogen carbonate solution was added, and extracted with ethyl acetate. The organic layer was dried over sodium sulfate, and concentrated under reduced pressure. The residue was subjected to silica gel column chromatography to give 0.79 g of the compound of the formula:

(Compound 13)

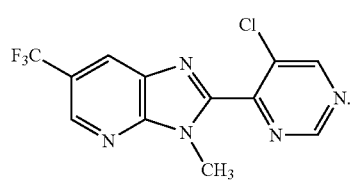

Production Example 7

To a mixture of 60% of sodium hydride (in oil) (0.04 g) and DMF (6 ml), 2,2,2-trifluoroethanol (0.05 g) was added dropwise under ice-cooling, and the reaction mixture was stirred for 5 minutes. After Compound 13 (0.12 g) was added, the reaction mixture was stirred at room temperature for 30 minutes. To the reaction mixture, water was added, and extracted with ethyl acetate. The organic layer was dried over sodium sulfate, and concentrated under reduced pressure. The residue was subjected to silica gel column chromatography to give 0.14 g of the compound of the formula:

(Compound 3)

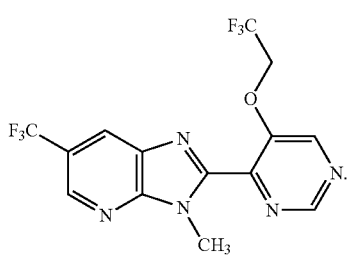

Production Example 8

To a mixture of Compound 13 (0.36 g) and DMF (20 ml), sodium ethyl mercaptanate (0.34 g) was added under ice-cooling, and the reaction mixture was stirred at room temperature for 3 hours. To the reaction mixture, water was added, and the precipitated solids were collected by filtration. The solid was washed with water, and dried to give 0.35 g of the compound of the formula:

(Compound 4)

Production Example 9

To a mixture of Compound 4 (0.24 g) and chloroform (20 ml), 69-75% of 3-chloroperbenzoic acid (0.28 g) was added under ice-cooling, and the reaction mixture was stirred at room temperature for 3.5 hours. Then, to the reaction mixture, saturated aqueous sodium hydrogen carbonate solution was added, and extracted with chloroform. The organic layer was dried over magnesium sulfate, and concentrated under reduced pressure. The residue was subjected to silica gel column chromatography to give 0.09 g of the compound of the formula:

(Compound 5)

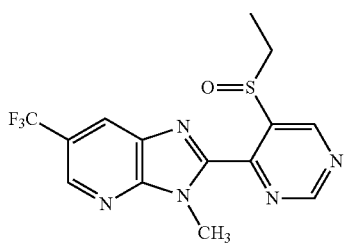

and 0.13 g of the compound of the formula:

(Compound 6)

Production Example 10

A mixture of 2-amino-4-trifluoromethyl-phenol (0.27 g), 5-ethyl-pyrimidine-4-carboxylic acid (0.27 g), WSC (0.25 g), and pyridine (5 ml) was stirred at 80° C. for 1 hour, at 100 for 1.5 hours, and at 115° C. for 0.5 hours. After standing to cool the reaction mixture to room temperature, to the reaction mixture, water was added, and extracted with ethyl acetate. The organic layer was dried over magnesium sulfate, and concentrated under reduced pressure. The residue was subjected to silica gel column chromatography to give 0.34 g of 5-ethyl-N-(2-hydroxy-5-trifluoromethyl-phenyl)-pyrimidine-4-carboxamide.

5-ethyl-N-(2-hydroxy-5-trifluoromethyl-phenyl)-pyrimidine-4-carboxamide $^1$H-NMR (CDCl$_3$) δ: 10.52 (1H, brs), 9.18 (1H, s), 8.87 (1H, s), 7.64 (1H, d), 7.43 (1H, dd), 7.13 (1H, d), 3.26 (2H, q), 1.35 (3H, t).

The compound (0.21 g) of the formula:

(Compound 10)

was produced according to Production Example 4, substituting 5-ethyl-N-(2-hydroxy-5-trifluoromethyl-pyridin-3-yl)-pyrimidine-4-carboxamide with 5-ethyl-N-(2-hydroxy-5-trifluoromethyl-phenyl)-pyrimidine-4-carboxamide.

The compounds produced by a similar production method to the above Production Examples are shown in the following table.

The compound of the formula (1):

(1)

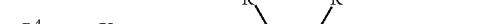

wherein R$^1$, R$^2$, R$^3$, R$^4$, R$^5$, X, Y, and Z represent a combination shown in Tables 12-13.

TABLE 12

| Compound | R¹ | R² | R³ | R⁴ | R⁵ | X | Y | Z |
|---|---|---|---|---|---|---|---|---|
| 1 | H | H | H | CF$_3$ | H | =CH— | =CH— | O |
| 2 | H | H | H | CF$_3$ | H | =CH— | =CH— | —N(CH$_3$)— |
| 3 | H | H | OCH$_2$CF$_3$ | CF$_3$ | H | =CH— | N | —N(CH$_3$)— |
| 4 | H | H | SCH$_2$CH$_3$ | CF$_3$ | H | =CH— | N | —N(CH$_3$)— |
| 5 | H | H | S(O)CH$_2$CH$_3$ | CF$_3$ | H | =CH— | N | —N(CH$_3$)— |
| 6 | H | H | S(O)$_2$CH$_2$CH$_3$ | CF$_3$ | H | =CH— | N | —N(CH$_3$)— |
| 7 | H | H | SCH$_2$CH$_3$ | CF$_3$ | H | =CH— | =CH— | —N(CH$_3$)— |
| 8 | H | H | S(O)CH$_2$CH$_3$ | CF$_3$ | H | =CH— | =CH— | —N(CH$_3$)— |
| 9 | H | H | S(O)$_2$CH$_2$CH$_3$ | CF$_3$ | H | =CH— | =CH— | —N(CH$_3$)— |
| 10 | H | H | CH$_2$CH$_3$ | CF$_3$ | H | =CH— | =CH— | O |
| 11 | H | H | CH$_2$CH$_3$ | CF$_3$ | H | =CH— | N | —N(CH$_3$)— |
| 12 | H | H | CH$_2$CH$_3$ | CF$_3$ | H | =CH— | =CH— | —N(CH$_3$)— |
| 13 | H | H | Cl | CF$_3$ | H | =CH— | N | —N(CH$_3$)— |
| 14 | H | H | Cl | CF$_3$ | H | =CH— | =CH— | —N(CH$_3$)— |
| 15 | H | H | CH$_2$CH$_3$ | CF$_3$ | H | =CH— | N | O |

TABLE 13

| Compound | R¹ | R² | R³ | R⁴ | R⁵ | X | Y | Z |
|---|---|---|---|---|---|---|---|---|
| 16 | H | H | Cl | SCF$_3$ | H | =CH— | N | —N(CH$_3$)— |
| 17 | H | H | SCH$_2$CH$_3$ | SCF$_3$ | H | =CH— | N | —N(CH$_3$)— |
| 18 | H | H | S(O)CH$_2$CH$_3$ | SCF$_3$ | H | =CH— | N | —N(CH$_3$)— |
| 19 | H | H | S(O)$_2$CH$_2$CH$_3$ | SCF$_3$ | H | =CH— | N | —N(CH$_3$)— |
| 20 | H | H | Cl | CF$_2$CF$_3$ | H | =CH— | N | —N(CH$_3$)— |
| 21 | H | H | SCH$_2$CH$_3$ | CF$_2$CF$_3$ | H | =CH— | N | —N(CH$_3$)— |
| 22 | H | H | S(O)CH$_2$CH$_3$ | CF$_2$CF$_3$ | H | =CH— | N | —N(CH$_3$)— |
| 23 | H | H | S(O)$_2$CH$_2$CH$_3$ | CF$_2$CF$_3$ | H | =CH— | N | —N(CH$_3$)— |
| 24 | H | H | OCH$_2$CH$_3$ | CF$_3$ | H | =CH— | =CH— | —N(CH$_3$)— |

The $^1$H-NMR data of the compounds listed in Tables 12-13 are shown below.

Compound 1
$^1$H-NMR (CDCl$_3$) δ: 7.78 (1H, d), 7.83 (1H, d), 8.18 (1H, s), 8.31 (1H, dd), 9.05 (1H, d), 9.49 (1H, d).

Compound 2
$^1$H-NMR (CDCl$_3$) δ: 9.35 (1H, d), 8.93 (1H, d), 8.42-8.40 (1H, m), 8.15-8.14 (1H, m), 7.66-7.63 (1H, m), 7.57 (1H, d), 4.40 (3H, s).

Compound 3
$^1$H-NMR (CDCl$_3$) δ: 9.19 (1H, s), 8.81 (1H, s), 8.79 (1H, m), 8.41 (1H, m), 4.72-4.66 (2H, m), 4.15 (3H, s).

Compound 4
$^1$H-NMR (CDCl$_3$) δ: 9.12 (1H, s), 8.85 (1H, s), 8.79 (1H, m), 8.46 (1H, m), 4.23 (3H, s), 3.10 (2H, q), 1.43 (3H, t).

Compound 5
$^1$H-NMR (CDCl$_3$) δ: 9.59 (1H, s), 9.48 (1H, s), 8.83 (1H, m), 8.40 (1H, m), 4.45 (3H, s), 3.70-3.65 (1H, m), 3.25-3.20 (1H, m), 1.54-1.48 (3H, m).

Compound 6
$^1$H-NMR (CDCl$_3$) δ: 9.60 (1H, s), 9.52 (1H, s), 8.81 (1H, d), 8.36 (1H, d), 4.04 (3H, s), 4.04-3.99 (2H, m), 1.45 (3H, t).

Compound 7
$^1$H-NMR (CDCl$_3$) δ: 9.09 (1H, s), 8.81 (1H, s), 8.24-8.22 (1H, m), 7.67-7.63 (1H, m), 7.56 (1H, d), 4.13 (3H, s), 3.07 (2H, q), 1.41 (3H, t).

Compound 8
$^1$H-NMR (CDCl$_3$) δ: 9.55 (1H, s), 9.43 (1H, s), 8.15-8.13 (1H, m), 7.72-7.68 (1H, m), 7.62 (1H, d), 4.39 (3H, s), 3.77-3.67 (1H, m), 3.28-3.18 (1H, m), 1.52 (3H, t).

Compound 9
$^1$H-NMR (CDCl$_3$) δ: 9.57 (1H, s), 9.49 (1H, s), 8.13-8.10 (1H, m), 7.70-7.66 (1H, m), 7.59 (1H, d), 4.05 (2H, q), 3.95 (3H, s), 1.44 (3H, t).

Compound 10
$^1$H-NMR (CDCl$_3$) δ: 9.32 (1H, s), 8.90 (1H, s), 8.21-8.19 (1H, m), 7.83 (1H, d), 7.78-7.74 (1H, m), 3.37 (2H, q), 1.40 (3H, t).

Compound 11
$^1$H-NMR (CDCl$_3$) δ: 9.25 (1H, s), 8.88 (1H, s), 8.77 (1H, m), 8.38 (1H, m), 4.15 (3H, s), 3.13 (2H, q), 1.29 (3H, t).

Compound 12
$^1$H-NMR (CDCl$_3$) δ: 9.22 (1H, s), 8.85 (1H, s), 8.16-8.14 (1H, m), 7.67-7.63 (1H, m), 7.56 (1H, d), 4.04 (3H, s), 3.11 (2H, q), 1.25 (3H, t).

Compound 13
$^1$H-NMR (CDCl$_3$) δ: 9.29 (1H, s), 9.02 (1H, s), 8.81 (1H, d), 8.45 (1H, d), 4.13 (3H, s).

Compound 14
$^1$H-NMR (CDCl$_3$) δ: 9.26 (1H, s), 8.99 (1H, s), 8.23-8.20 (1H, m), 7.70-7.65 (1H, m), 7.58 (1H, d), 4.03 (3H, s).

Compound 15
$^1$H-NMR (CDCl$_3$) δ: 9.35 (1H, s), 8.93 (1H, s), 8.82 (1H, d), 8.49 (1H, d), 3.33 (2H, q), 1.41 (3H, t).

Compound 16
$^1$H-NMR (CDCl$_3$) δ: 9.28 (1H, s), 9.02 (1H, s), 8.75 (1H, d), 8.51 (1H, d), 4.11 (3H, s).

Compound 17
$^1$H-NMR (CDCl$_3$) δ: 9.11 (1H, s), 8.84 (1H, s), 8.72 (1H, s), 8.52 (1H, s), 4.21 (3H, s), 3.10 (2H, q), 1.43 (3H, t).

Compound 18
$^1$H-NMR (CDCl$_3$) δ: 9.58 (1H, s), 9.47 (1H, s), 8.77 (1H, d), 8.47 (1H, d), 4.43 (3H, s), 3.74-3.60 (1H, m), 3.30-3.17 (1H, m), 1.50 (3H, t).

Compound 19
$^1$H-NMR (CDCl$_3$) δ: 9.59 (1H, s), 9.51 (1H, s), 8.75 (1H, d), 8.42 (1H, d), 4.07-3.97 (5H, m), 1.45 (3H, t)

Compound 20
$^1$H-NMR (CDCl$_3$) δ: 9.29 (1H, s), 9.02 (1H, s), 8.75 (1H, d), 8.43 (1H, d), 4.13 (3H, s).

Compound 21
$^1$H-NMR (CDCl$_3$) δ: 9.12 (1H, s), 8.85 (1H, s), 8.73 (1H, s), 8.44 (1H, s), 4.23 (3H, s), 3.19-3.03 (2H, m), 1.48-1.38 (3H, m).

Compound 22

$^1$H-NMR (CDCl$_3$) δ: 9.59 (1H, s), 9.48 (1H, s), 8.78 (1H, s), 8.37 (1H, s), 4.45 (3H, s), 3.74-3.61 (1H, m), 3.31-3.18 (1H, m), 1.53-1.46 (3H, m).

Compound 23

$^1$H-NMR (CDCl$_3$) δ: 9.60 (1H, s), 9.52 (1H, s), 8.76 (1H, d), 8.33 (1H, d), 4.06-3.97 (5H, m), 1.45 (3H, t).

Compound 24

$^1$H-NMR (CDCl$_3$) δ: 9.14 (1H, s), 8.75 (1H, s), 8.15-8.13 (1H, m), 7.66-7.62 (1H, m), 7.55-7.53 (1H, m), 4.63 (2H, q), 4.04 (3H, s).

Formulation Examples are shown below. The "part" is based on by weight.

Formulation Example 1

Any one of Compounds 1-24 (10 parts) is dissolved in a mixture of xylene (35 parts) and N,N-dimethylformamide (35 parts), and to the mixture is added polyoxyethylene styryl phenyl ether (14 parts) and calcium dodecylbenzenesulfonate (6 parts), and stirred to give emulsions of each compound.

Formulation Example 2

Sodium lauryl sulfate (4 parts), calcium lignin sulfonate (2 parts), synthetic hydrated silicone oxide powder (20 parts) and diatomite (54 parts) are mixed, then to the mixture is added any one of Compounds 1-24 (20 parts), and mixed to give wettable powders of each compound.

Formulation Example 3

To any one of Compounds 1-24 (2 parts) is added synthetic hydrated silicone oxide powder (1 part), calcium lignin sulfonate (2 parts), bentonite (30 parts), and kaolin clay (65 parts), and mixed. Then, to the mixture is added an appropriate amount of water, further stirred, granulated with a granulator, and draft-dried to give granules of each compound.

Formulation Example 4

Any one of Compounds 1-24 (1 part) is dissolved in an appropriate amount of acetone. To the mixture is added synthetic hydrated silicone oxide powder (5 parts), PAP (0.3 parts), and Fubasami clay (93.7 parts), and well stirred. Then, acetone is removed by evaporation to give powders of each compound.

Formulation Example 5

A mixture (ratio by weight=1:1) of polyoxyethylene alkyl ether sulfate ammonium salt and white carbon (35 parts), any one of Compounds 1-24 (10 parts), and water (55 parts) are mixed, pulverized by a wet grinding method to give formulations of each compounds.

Formulation Example 6

Any one of Compounds 1-24 (0.1 parts) is dissolved in xylene (5 parts) and trichloroethane (5 parts), and mixed with deodorized kerosene (89.9 parts) to give oil solutions of each compounds.

Formulation Example 7

Any one of Compounds 1-24 (10 mg) is dissolved in acetone (0.5 ml). The mixture is added to animal powdered solid feed (powdered solid feed for breeding, CE-2, from CLEA Japan, Inc.), (5 g) and mixed uniformly. Then, acetone is removed by evaporation to give poison baits of each compound.

Formulation Example 8

Any one of Compounds 1-24 (0.1 parts) and Neothiosol (Chuo Kasei Co. Ltd.) (49.9 parts) are charged into an aerosol container. After an aerosol valve is attached to the container, dimethyl ether (25 parts) and LPG (25 parts) are charged into the container. The container is vibrated, and attaching an actuator to give oily aerosols of each compound.

Formulation Example 9

Any one of Compounds 1-24 (0.6 parts), BHT (2,6-di-tert-butyl-4-methylphenol) (0.01 parts), xylene (5 parts), deodorized kerosene (3.39 parts), and an emulsifier (Atmos 300 (a registered trade name for Atmos Chemical Ltd.)) (1 part) are mixed and dissolved. The mixture and distilled water (50 parts) are charged into an aerosol container, and attaching a valve. Then, propellant (LPG) (40 parts) is pressure-charged into the container through the valve to give aqueous aerosols of each compound.

The effects of the present compounds to control pests are shown in Test Examples.

Test Example 1

The test spray solutions were prepared by diluting the formulations of each of Compounds 1-13 and 15-24 obtained in Formulation Example 5 with water so as to give 500 ppm of an active ingredient concentration.

On the other hand, about 30 *Aphis gossypii* were incubated on a cucumber seeding (the first true leaf stage) planted in a plastic cup, and leaving it for a day. 20 ml of each of the above test spray solutions was sprayed on this seeding.

Six days after spraying, the number of the surviving *Aphis gossypii* parasitized on the leaves of the cucumber was examined, and a control value was calculated according to the following equation:

$$\text{Control value}(\%) = \{1 - (Cb \times Tai)/(Cai \times Tb)\} \times 100$$

wherein symbols represent as follows:

Cb: the number of insects in a non-treated section before treatment,

Cai: the number of insects in a non-treated section in observation,

Tb: the number of insects in a treated-section before treatment,

Tai: the number of insects in a treated-section in observation.

As a result, in the treated-section of the test spray solution of each of Compounds 1-13 and 15-24, the control value of 90% or more was shown.

Test Example 2

The test spray solutions were prepared by diluting the formulations of each of Compounds 2-13 and 15-24 obtained in Formulation Example 5 with water so as to give 500 ppm of an active ingredient concentration.

On the other hand, *Bemisia tabaci* adult was released on a tomato seeding (the third true leaf stage) planted in a polyethylene cup, and made to lay eggs for about 24 hours. The tomato seedling was kept in a greenhouse for 8 days. When instar larvae hatched from the eggs, the above test spray solution was sprayed in the amount of 10 ml/cup. The cup was kept in a greenhouse at 25° C. After the keeping for 7 days, the number of surviving instar larvae on the tomato leaves was examined, and a control value was calculated according to the following equation:

Control value(%)={1−(Cb×Tai)/(Cai×Tb)}×100 wherein symbols represent as follows:
Cb: the number of pests in a non-treated section before treatment,
Cai: the number of pests in a non-treated section in observation,
Tb: the number of pests in a treated-section before treatment,
Tai: the number of pests in a treated-section in observation.

As a result, in the treated-section of the test spray solution of each of Compounds 2-13 and 15-24, the control value of 90% or more was shown.

INDUSTRIAL APPLICABILITY

The present compound has a control effect against pests and is useful as an active ingredient of a pest controlling agent.

The invention claimed is:
1. A pyrimidine compound of the formula (1):

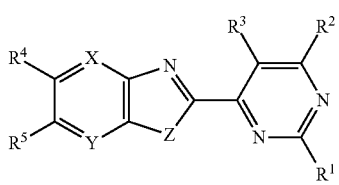

wherein:
$R^1$ represents hydrogen or halogen,
$R^2$ represents hydrogen or halogen,
$R^3$ represents a C1-C6 chain hydrocarbon group optionally having one or more halogens, a C3-C8 cycloalkyl group optionally having one or more halogens, a C1-C6 alkoxy group optionally having one or more halogens, a C1-C6 alkylthio group optionally having one or more halogens, a C1-C6 alkylsulfinyl group optionally having one or more halogens, a C1-C6 alkylsulfonyl group optionally having one or more halogens, a C1-C6 alkylamino group optionally having one or more halogens, a C2-C8 dialkylamino group optionally having one or more halogens, a C2-C6 alkylcarbonylamino group optionally having one or more halogens, a C2-C6 alkoxycarbonylamino group optionally having one or more halogens, a C2-C6 alkylcarbonyl group optionally having one or more halogens, a C2-C6 alkoxycarbonyl group optionally having one or more halogens, a C2-C6 alkylcarbamoyl group optionally having one or more halogens, a C2-C8 dialkylcarbamoyl group optionally having one or more halogens, a C2-C6 alkoxyalkyl group optionally having one or more halogens, a C2-C6 alkylthioalkyl group optionally having one or more halogens, a phenyl group optionally having one or more atoms or groups selected from Group α, a 5-6 membered aromatic heterocyclic group optionally having one or more atoms or groups selected from Group α, hydrogen, halogen, a hydroxyl group, a mercapto group, an amino group, a nitro group, a cyano group, or a formyl group,
$R^4$ and $R^5$ may be same or different and independently represent a C1-C6 chain hydrocarbon group optionally having one or more halogens, a C3-C8 cycloalkyl group optionally having one or more halogens, a C1-C6 alkoxy group optionally having one or more halogens, a C1-C6 alkylthio group optionally having one or more halogens, a C1-C6 alkylsulfinyl group optionally having one or more halogens, a C1-C6 alkylsulfonyl group optionally having one or more halogens, a C1-C6 alkylamino group optionally having one or more halogens, a C2-C8 dialkylamino group optionally having one or more halogens, a C2-C6 alkylcarbonyl group optionally having one or more halogens, a C2-C6 alkoxycarbonyl group optionally having one or more halogens, a phenyl group optionally having one or more atoms or groups selected from Group α, a 5-6 membered aromatic heterocyclic group optionally having one or more atoms or groups selected from Group α, hydrogen, halogen, a hydroxyl group, a mercapto group, an amino group, a nitro group, a cyano group, or a formyl group, provided that both $R^4$ and $R^5$ are not hydrogen; or $R^4$ and $R^5$ may together with the atom to which they are bonded form a 5- or 6-membered ring having one or more halogens,
X represents nitrogen or =$CR^6$— wherein $R^6$ represents hydrogen or halogen,
Y represents nitrogen or =$CR^7$— wherein $R^7$ represents hydrogen or halogen,
Z represents oxygen or —$NR^8$— wherein $R^8$ represents a C1-C6 chain hydrocarbon group optionally having one or more halogens, a C3-C8 cycloalkyl group optionally having one or more halogens, or hydrogen; and
the Group α consists of a C1-C3 alkyl group optionally having one or more halogens, a C1-C3 alkoxy group optionally having one or more halogens, halogen, a cyano group, and a nitro group.

2. The pyrimidine compound according to claim 1 wherein $R^1$ is hydrogen, and $R^2$ is hydrogen.

3. The pyrimidine compound according to claim 1 wherein $R^3$ is a C1-C6 chain hydrocarbon group optionally having one or more halogens, a C1-C6 alkoxy group optionally having one or more halogens, a C1-C6 alkylthio group optionally having one or more halogens, a C1-C6 alkylsulfinyl group optionally having one or more halogens, a C1-C6 alkylsulfonyl group optionally having one or more halogens, hydrogen, or halogen.

4. The pyrimidine compound according to claim 1 wherein $R^3$ is a C1-C3 alkyl group optionally having one or more halogens, a C1-C3 alkoxy group optionally having one or more halogens, a C1-C3 alkylthio group optionally having one or more halogens, a C1-C3 alkylsulfinyl group optionally having one or more halogens, a C1-C3 alkylsulfonyl group optionally having one or more halogens, hydrogen, or halogen.

5. The pyrimidine compound according to claim 1 wherein $R^3$ is a C1-C3 alkylthio group optionally having one or more halogens, a C1-C3 alkylsulfinyl group optionally having one or more halogens, or a C1-C3 alkylsulfonyl group optionally having one or more halogens.

6. The pyrimidine compound according to claim 1 wherein $R^4$ is a C1-C3 alkyl group optionally having one or more halogens, a C1-C3 alkoxy group optionally having one or more halogens, a C1-C3 alkylthio group optionally having one or more halogens, halogen, a hydroxyl group, a mercapto group, a nitro group, or a cyano group, and $R^5$ is hydrogen.

7. The pyrimidine compound according to claim 1 wherein $R^4$ is a C1-C3 alkyl group having one or more fluorines, a C1-C3 alkoxy group having one or more fluorines, a C1-C3 alkylthio group having one or more fluorines, chlorine, or bromine, and $R^5$ is hydrogen.

8. The pyrimidine compound according to claim 1 wherein Z is oxygen, X is =$CR^6$—, and $R^6$ is hydrogen.

9. The pyrimidine compound according to claim 1 wherein Z is —$NR^8$—, $R^8$ is a methyl group, X is =$CR^6$—, and $R^6$ is hydrogen.

10. The pyrimidine compound according to claim 1 wherein Y is nitrogen.

11. A pest controlling agent comprising the pyrimidine compound according to claim 1 and an inert carrier.

12. A method of controlling pests which comprises the step of applying an effective amount of the pyrimidine compound according to claim 1 to pests or habitats of pests.

* * * * *